United States Patent
Pias et al.

(10) Patent No.: US 12,121,205 B2
(45) Date of Patent: Oct. 22, 2024

(54) FLUORESCENCE CALIBRATION BASED ON MANUAL LUMEN DETECTION

(71) Applicant: CANON U.S.A., INC., Melville, NY (US)

(72) Inventors: Matthew Scott Pias, Brookline, MA (US); Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 416 days.

(21) Appl. No.: 17/493,184

(22) Filed: Oct. 4, 2021

(65) Prior Publication Data

US 2023/0109202 A1   Apr. 6, 2023

(51) Int. Cl.
*A61B 1/00*   (2006.01)
*A61B 1/04*   (2006.01)
(Continued)

(52) U.S. Cl.
CPC ........ *A61B 1/00057* (2013.01); *A61B 1/0005* (2013.01); *A61B 1/043* (2013.01);
(Continued)

(58) Field of Classification Search
CPC ..... A61B 1/043; A61B 1/0638; A61B 5/0066; A61B 1/00057
See application file for complete search history.

(56) References Cited

U.S. PATENT DOCUMENTS

| 8,052,605 B2 | 11/2011 | Muller et al. |
| 9,557,154 B2 | 1/2017 | Tearney et al. |

(Continued)

FOREIGN PATENT DOCUMENTS

| JP | 2007-222381 A | 9/2007 |
| JP | 2019-088771 A | 6/2019 |

(Continued)

OTHER PUBLICATIONS

Wang, H., et al., "Ex vivo catheter-based imaging of coronary atherosclerosis using multimodality OCT and NIRAF excited at 633 nm," Biomedical Optics Express, Apr. 1, 2015, pp. 1363-1375, vol. 6, No. 4.

(Continued)

*Primary Examiner* — Oommen Jacob
(74) *Attorney, Agent, or Firm* — Canon U.S.A., Inc., IP Division

(57) ABSTRACT

A method and system for calibrating fluorescence data in a multimodality image acquired from a vessel imaged by an imaging catheter. A fluorescence signal acquired by a first modality is calibrated by applying a first calibration factor based on a lumen distance and/or radiation angle from the catheter to the vessel wall. If a parameter of the calibrated fluorescence signal is different from a predetermined condition, a user is prompted to manually select a lumen boundary and/or a region of interest (ROI) on the image of the vessel. An optical attenuation property of the selected boundary and/or ROI is calculated based on backscattered radiation collected by a second modality, and the fluorescence signal is further calibrated by applying a second calibration factor based on the optical attenuation property.

19 Claims, 6 Drawing Sheets

(51) Int. Cl.
  *A61B 1/06* (2006.01)
  *A61B 1/313* (2006.01)
  *A61B 5/00* (2006.01)
(52) U.S. Cl.
  CPC .......... *A61B 1/0638* (2013.01); *A61B 1/3137* (2013.01); *A61B 5/0066* (2013.01)

(56) References Cited

U.S. PATENT DOCUMENTS

| | | | |
|---|---|---|---|
| 10,338,795 | B2 | 7/2019 | Gopinath et al. |
| 10,952,616 | B2* | 3/2021 | Watanabe ........... G01N 21/4795 |
| 2003/0028100 | A1 | 2/2003 | Tearney et al. |
| 2007/0158585 | A1 | 7/2007 | Hall et al. |
| 2009/0036770 | A1 | 2/2009 | Tearney et al. |
| 2009/0043192 | A1 | 2/2009 | Tearney et al. |
| 2012/0101374 | A1 | 4/2012 | Tearney et al. |
| 2015/0213629 | A1 | 7/2015 | Celi et al. |
| 2016/0228097 | A1* | 8/2016 | Jaffer ................... A61B 8/4416 |
| 2017/0020392 | A1 | 1/2017 | Xu |
| 2017/0156599 | A1 | 6/2017 | Kemp et al. |
| 2018/0271614 | A1 | 9/2018 | Kunio |
| 2019/0029624 | A1 | 1/2019 | Kunio |
| 2019/0099079 | A1* | 4/2019 | Yamada ............... A61B 5/0071 |
| 2019/0099080 | A1 | 4/2019 | Kunio et al. |
| 2019/0298174 | A1* | 10/2019 | Watanabe ........... A61B 5/0066 |
| 2019/0339850 | A1 | 11/2019 | Ho |
| 2020/0085285 | A1* | 3/2020 | Yamada ............. A61B 1/00057 |
| 2020/0205750 | A1 | 7/2020 | Begin et al. |
| 2020/0294659 | A1 | 9/2020 | Gopinath et al. |
| 2020/0352446 | A1 | 11/2020 | Petroff et al. |
| 2020/0402646 | A1 | 12/2020 | Nickisch et al. |
| 2021/0113098 | A1 | 4/2021 | Yamada et al. |
| 2021/0121132 | A1 | 4/2021 | Watanabe et al. |
| 2021/0161387 | A1 | 6/2021 | Wang et al. |
| 2023/0109202 | A1* | 4/2023 | Pias .................... A61B 1/3137 600/425 |

FOREIGN PATENT DOCUMENTS

| | | |
|---|---|---|
| JP | 2019-207222 A | 12/2019 |
| JP | 2021-090723 A | 6/2021 |

OTHER PUBLICATIONS

Ughi, G.J., et al., "Dual modality intravascular optical coherence tomography (OCT) and near-infrared fluorescence (NIRF) imaging: a fully automated algorithm for the distance-calibration of NIRF signal intensity for quantitative molecular imaging", Int J Cardiovasc Imaging. Feb. 2015, pp. 259-268, vol. 31, No. 2).

Liu, S., et al., "Tissue characterization with depth-resolved attenuation coefficient and backscatter term in intravascular optical coherence tomography images," J. Biomed. Opt., Sep. 12, 2017, vol. 22, No. 9.

Cheimariotis, G.A., et al., "ARC-OCT: Automatic detection of lumen border in intravascular OCT images", Computer Methods and Programs in Biomedicine, 2017, pp. 21-32, vol. 151.

Utzinger, U., et al., "Fiber optic probes for biomedical optical spectroscopy", Journal of Biomedical Optics, Jan. 2003, pp. 121-147, vol. 6, No. 1.

Nam, H., et al., "Automated detection of vessel lumen and stent struts in intravascular optical coherence tomography to evaluate stent appostition and neointimal coverage", Med. Phys. Apr. 2016, pp. 1662-1675, vol. 43, No. 4.

Yoo, H., et al., "Intra-arterial catheter for simultaneous microstructural and molecular imaging in vivo", Nat. Med., Jun. 1, 2012, pp. 1680-1684, vol. 17, No. 12.

Ramanujam, N., "Fluorescence Spectroscopy of Neoplastic and Non-Neoplastic Tissues", Neoplasia, Jan.-Apr. 2000, pp. 89-117, vol. 2, Nos. 1-2.

* cited by examiner

OCT overlay

NIRAF overlay

FLUORESCENCE CALIBRATION BASED ON MANUAL LUMEN DETECTION

CROSS-REFERENCE TO RELATED APPLICATIONS n/a

BACKGROUND INFORMATION

Field of Disclosure

The present disclosure generally relates to medical imaging. More particularly, this disclosure is directed to a system and method of image processing and signal calibration of medical images acquired from inside a biological lumen with a multi-modality imaging catheter.

Description of Related Art

Biological tissues consist of heterogeneous structures such as chromophores that absorb light and fluorophores that fluoresce (i.e., absorb and reemit light). For this reason, when light interacts with biological tissue, light diffuses within the tissue structures and can be absorbed, reflected, reemitted, and/or scattered. These optical processes allow imaging techniques to characterize the tissue structure and identify diseases by noninvasive or minimally invasive imaging methods. Optical coherence tomography (OCT) imaging is an imaging technique that uses near-infrared light to provide high-resolution, cross-sectional morphological information of tissue microstructures in situ and in real-time. In OCT, a laser beam scans across the tissue surface of a sample to acquire a two- or three-dimensional image. This technique is commonly used in ophthalmology and in cardiology. For cardiovascular applications, the OCT light beam is transmitted through a catheter that is advanced into the coronary arteries of a patient being treated for coronary artery disease (CAD). The imaging beam emitted from the catheter distal end is swept along the vessel wall in a rotary fashion, while the catheter is pulled back inside the artery to collect image data from the vessel over a length of about 5-10 centimeters (cm). Image processing of the resulting data set can show complex coronary conditions and vessel-wall pathologies such as atherosclerosis, with a resolution of approximately 10 microns (µm). Typical OCT image processing includes image segmentation, feature quantification, object detection, and tissue characterization.

Intravascular fluorescence is a catheter-based molecular imaging technique that uses laser light to stimulate fluorescence emission from a vessel wall and/or from plaque components within a particular vessel. Fluorescence may include near-infrared auto-fluorescence (NIRAF) generated by endogenous fluorophores, or near-infrared fluorescence (NIRF) generated by molecular agents injected intravenously in the vessel. Fluorescence detection can be obtained by integrating the emitted intensity of fluorescence over a short period of time, by measuring the life-time of the fluorescence signal (i.e., fluorescence-lifetime imaging microscopy or FLIM), or by analyzing the spectral shape of emitted fluorescence (fluorescence spectroscopy). Near-infrared light is often used to stimulate fluorescence emission in the case of intravascular applications. Imaging catheters contain an optical fiber to deliver and collect light to and from the lumen of a vessel through semi-invasive interventions (e.g., percutaneous coronary intervention in case of coronary arteries).

The integration of OCT and fluorescence imaging modalities into a single imaging catheter provides a multimodality OCT system (MMOCT system) with the capability to simultaneously obtain co-localized anatomical and molecular information from a lumen sample such as an artery. See, for example, publications by Wang et al., (herein "Wang") entitled "*Ex vivo catheter-based imaging of coronary atherosclerosis using multimodality OCT and NIRAF excited at 633 nm,*" Biomedical Optics Express 6(4), 1363-1375 (2015); Ughi et al., (herein "Ughi") entitled "*Dual modality intravascular optical coherence tomography (OCT) and near-infrared fluorescence (NIRF) imaging: a fully automated algorithm for the distance-calibration of NIRF signal intensity for quantitative molecular imaging. Int J Cardiovasc Imaging.* 2015 February; 31(2):259-68; and patent-related publications including U.S. Pat. No. 9557154, US 20160228097, US 20190099079, and US 20190298174, among others.

In a MMOCT system, the detected signal strength of fluorescence depends on the distance between the catheter and the lumen edge (the "lumen distance"), and/or on the angle of radiation incident on the lumen (the "incidence angle"). In that regard, it is known that the detected fluorescence signal is strong when the lumen distance is short, and becomes weaker as the distance from the imaging probe to the lumen wall becomes relatively large. It is also known that when the catheter is too close to the lumen edge (e.g., touching the wall of the vessel), the detected fluorescence signal can be inaccurate (i.e., the detected fluorescence can be a false positive signal). In the current state of the art, the system disclosed by Wang, for example, uses the OCT modality to measure the lumen distance, and calibrates the intensity of the fluorescence signal collected by the imaging probe using a calibration factor based the distance between the optical probe and the tissue. In addition, patent application publication US 2019/0099079 (disclosed by the Assignee of the present application) uses the OCT modality to measure the incident angle at axial and longitudinal planes, and calibrates the intensity of the fluorescence signal collected by the imaging probe using a calibration factor based on the calculated angles of incidence. However, it has been found that collection efficiency of a fluorescence signal depends not only on the lumen distance and/or incident angle of radiation, but also on one or more optical properties such as the optical attenuation property and/or scattering property of tissue heterogeneities. See, for example, Liu et al., (Liu), "*Tissue characterization with depth-resolved attenuation coefficient and backscatter term in intravascular optical coherence tomography images,*" J. Biomed. Opt. 22(9) 096004 (12 Sep. 2017). See also patent application publications US 2003/0028100, US 2009/0036770, US 2009/0043192 and US 2021/0161387, which are incorporated by reference herein in their entirety.

In other words, the current state of the art proposes that calibration of a fluorescence signal should be based on one or more parameters including the distance from catheter to lumen wall, the incident angle of radiation, and the depth of signal and tissue composition which are generally denoted as the "path of travel". These parameters are typically derived from a morphological image generated using a structural modality such as OCT or intravascular ultrasound (IVUS).

In this regard, it should be noted that fluorophores can be located at varying depths in the vessel wall and in plaques built-up at various locations of the vessel. However, in the method for calibration of NIRAF using distance to lumen wall and incident angle alone, the current state-of-the art assumes that fluorophores are located superficially on the lumen wall. In order to accurately characterize the fluorophore, not only the lumen wall alone, but also the lumen morphology and its location must be known to calibrate the NIRAF signal attenuation as a function of the signal path length to the fluorophore.

In the current state of the art, automatic lumen detection is chiefly relied upon to determine the signal path length from catheter to lumen. However, if automatic detection of the lumen surface, depth of signal, and angle of irradiation are inaccurate, the resulting synchronization and calibration of the imaging signals will be inaccurate as well. Automatic lumen detection accuracy suffers in vessels that have irregular lumen shapes, non-uniform composition of lumen walls, and where the lumen wall distance from the optical probe varies radially. In this environment, reliance solely on automatic lumen detection can potentially lead to lower fidelity NIRAF calibration, and the NIRAF reconstruction predicated on this calibration can still be inaccurate, which can lead to erroneous diagnosis and/or treatments. Therefore, in addition to automated lumen detection, a method for manual lumen wall identification, selection of a fluorescent region, or partially automated segmentation and manual selection of regions of interest in the vessel relevant to NIRAF calibration would increase the fidelity of calibration and ensure more accurate diagnostic and/or treatment results.

SUMMARY OF EXEMPLARY EMBODIMENTS

According to at least one embodiment of the present disclosure, there is provided a MMOCT system and method for calibrating fluorescence data collected from a lumen sample using a multimodality imaging catheter. In one embodiment, a fluorescence signal acquired by a first modality is calibrated by applying a first calibration factor based on a lumen distance and/or incident angle from the catheter to the sample. If a parameter of the calibrated fluorescence signal is different from a predetermined condition, a user is prompted to manually select a boundary and/or region of interest (ROI) of the sample. An optical attenuation property of the selected boundary and/or ROI is calculated based on backscattered radiation collected by a second modality, and the fluorescence signal is further calibrated by applying a second calibration factor based on the optical attenuation property.

According to another embodiment, a catheter-based multi-modality imaging system, comprises: a catheter configured to be inserted through a lumen of a vessel to guide radiation of two or more wavelengths to a vessel wall, and configured to simultaneously collect backscattered radiation in response to irradiating the vessel wall with a radiation of first wavelength and collect a fluorescence signal emitted by the vessel wall in response to irradiating the vessel wall with a radiation of second wavelength different from the first wavelength; and a processor. The process is configured to: display an image of the vessel by overlaying first data corresponding to the collected backscattered radiation and second data corresponding to the collected fluorescence signal, wherein the first data shows a lumen boundary of the vessel wall and the second data shows the fluorescence signal in radial relation to the lumen boundary; calculate, based on the first data, a lumen distance from the catheter to the vessel wall and/or an incident angle of the radiation incident on the vessel wall; and generate a first calibrated fluorescence signal by applying a first calibration factor to the fluorescence signal based on the lumen distance and/or the incident angle; wherein, if a parameter of the first calibrated fluorescence signal is different from a predetermined threshold value, the processor is further configured to: (i) prompt a user to select a portion of the lumen boundary and/or a region of interest (ROI) of the vessel wall, (ii) calculate an optical attenuation property of the selected portion of lumen boundary and/or of the selected ROI based on the backscattered radiation collected from the vessel wall, and (iii) generate a second calibrated fluorescence signal by applying a second calibration factor to the first calibrated fluorescence signal, the second calibration factor being based on the optical attenuation property of the selected portion of lumen boundary and/or of the selected ROI.

According to another embodiment, the processor is further configured to reconstruct an image of the vessel by combining data corresponding to the backscattered radiation and data corresponding to the first calibrated fluorescence signal and/or data corresponding to the second calibrated fluorescence signal, wherein the reconstructed image shows the data corresponding to the first calibrated fluorescence signal and/or the data corresponding to the second calibrated fluorescence signal in radial correspondence with the first image data only at radial locations where calibration of the fluorescence signal occurs.

According to a further embodiment, a method of calibrating a fluorescence signal using images acquired by a multimodality probe, comprises: irradiating a sample with a radiation of first wavelength using a first imaging modality; irradiating the sample with a radiation of second wavelength different from the radiation of first wavelength using a second imaging modality; simultaneously guiding the radiation of first and second wavelengths to the sample, and simultaneously collecting backscattered radiation in response to irradiating the sample with the radiation of first wavelength and a fluorescence signal emitted by the sample in response to irradiating the sample with the radiation of second wavelength using a catheter operatively coupled to the first and second imaging modalities; and processing, using a processor, the backscattered radiation and the fluorescence signal collected from the sample to: calculate, based on the backscattered radiation, a lumen distance between the catheter and the sample and/or an incident angle of the radiation incident on the sample; and generate a first calibrated fluorescence signal by applying a first calibration factor to the fluorescence signal based on the lumen distance and/or the incident angle. In a case where a parameter of the first calibrated fluorescence signal is different than a predetermined level, the processor is further configured to: (i) prompt a user to select a boundary and/or a region of interest (ROI) of the sample, (ii) calculate an optical attenuation property of the sample based on the backscattered radiation collected from the selected boundary and/or ROI, and (iii) generate a second calibrated fluorescence signal by applying a second calibration factor to the first calibrated fluorescence signal based on the optical attenuation property.

These and other objects, features, and advantages of the present disclosure will become apparent upon reading the following detailed description of exemplary embodiments of the present disclosure, when taken in conjunction with the appended drawings, and provided claims.

DETAILED DESCRIPTION OF EXEMPLARY EMBODIMENTS

Figure 1:
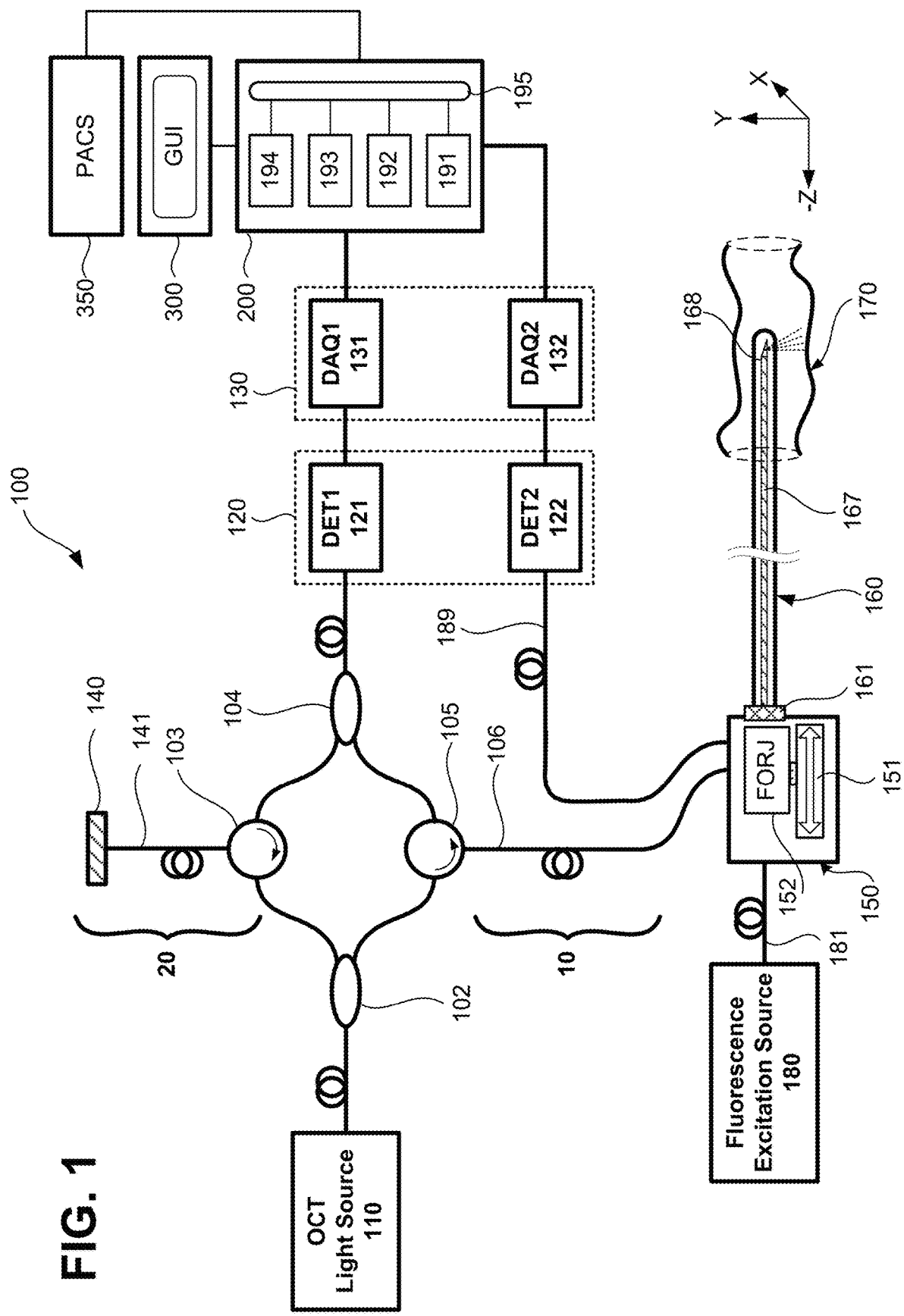
FIG. 1 illustrates an exemplary multimodality imaging system 100 including a fluorescence modality and an OCT modality using a common fiber-based imaging catheter 160.

Before the various embodiments are described in further detail, it is to be understood that the present disclosure is not limited to any particular embodiment. It is also to be understood that the terminology used herein is for the purpose of describing exemplary embodiments only, and is not intended to be limiting.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

As described in the Background section above, calibration of a detected fluorescence signal can be done via determination of a calibration factor based on the distance to the sample and/or the incident angle of radiation. The distance to the sample and/or the incident angle of radiation are typically obtained from a structural imaging modality such as OCT or IVUS. In this technique, the detected intensity of the fluorescence signal is multiplied by the calibration factor in order to calibrate the detected signal. To improve calibration accuracy, calibration can be done using the "depth" of the fluorescence signal obtained from OCT signal intensity profiles for varying depths of signal and composition of tissue, and defining a corresponding calibration function for each parameter. In IVUS-NIRS multi-modalities, calibration can be improved by using IVUS elastography and histology techniques, and then optionally combining them with the distance and/or angle measurements to determine a singular calibration factor. Most of these methods of calibration based on lumen distance, depth of signal, tissue composition, and incident angle can be combined and/or repurposed as workflow components in realizing the calibration techniques applied to the factors described in the present disclosure.

The present disclosure proposes certain illustrative embodiments of fluorescence calibration based on manual lumen detection and/or manual selection of one or more ROIs to improve measurement of optical parameters within selected regions of interest, although other embodiments may include alternatives, equivalents, and modifications. Additionally, the illustrative embodiments include several novel features that describe claimed subject matter, but certain particular features may not be essential to implement or practice the apparatuses, systems, and/or methods described herein.

<Multi-Modality Catheter System>

Figure 2A:
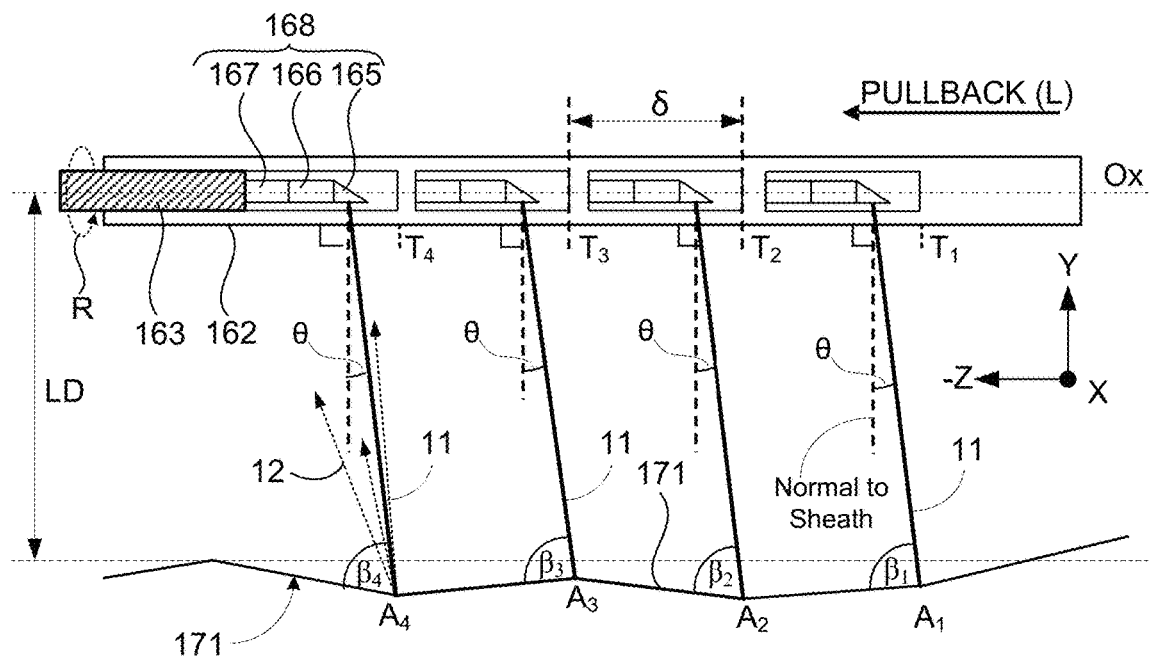
FIG. 2A and FIG. 2B respectively illustrate exemplary longitudinal and axial views of the catheter 160 at sequential positions during a pullback operation.
Figure 2B:
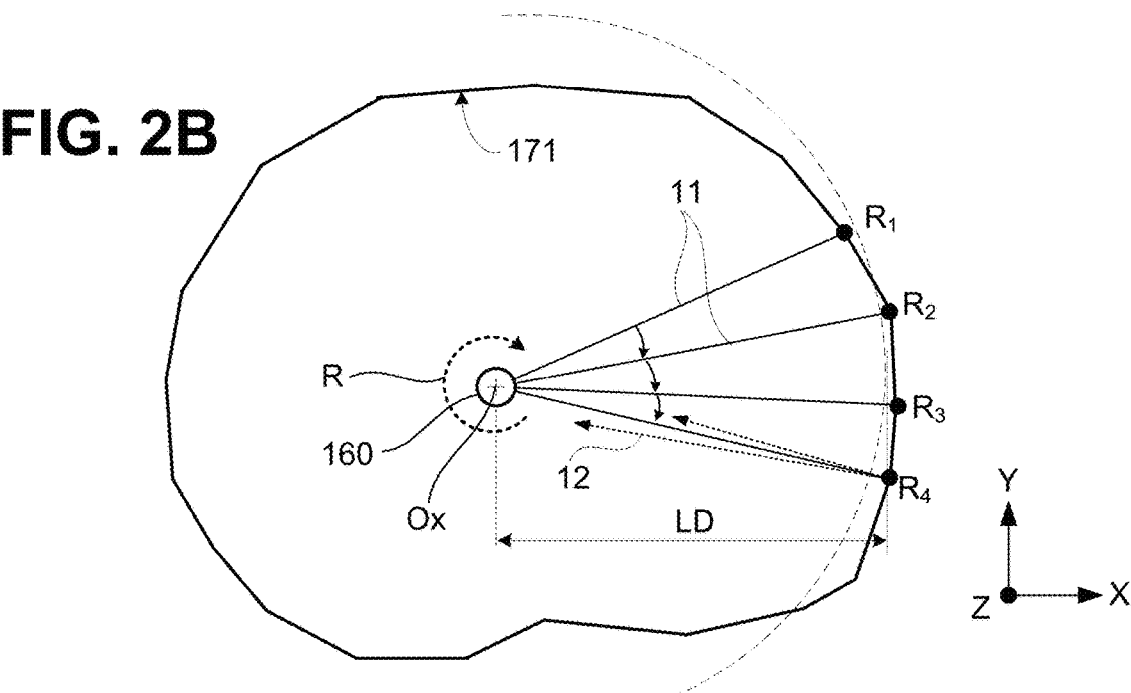

FIG. 1 illustrates an exemplary multimodality imaging system too including a fluorescence modality and an OCT modality using a common fiber-based imaging catheter 160. FIG. 2A and FIG. 2B respectively illustrate exemplary longitudinal and axial views of the catheter 160 at sequential positions during a pullback operation. The system 100 can be used as an intravascular imaging system configured to acquire images of coronary arteries or cerebral arteries. The system 100 may also be adapted with a balloon catheter or other appropriate structure to be used for imaging other bodily lumens, such as esophageal imaging or similar. As depicted in FIG. 1, the OCT modality is comprised of an interferometer having a sample arm 10 and a reference arm 20, an OCT light source 110, a detector unit 120, a data acquisition (DAQ) unit 130, and a computer system 200. The computer system 200 is connected to a display device 300 and an external system such as a picture archiving and communication system (PACS) 350. The sample arm to includes a patient interface unit (PIU) 150, and a fiber-based catheter 160. The fluorescence modality is comprised of an excitation light source 180, the catheter 160, an optical detector 183, the data acquisition (DAQ) unit 130, and the computer system 200. In other words, the OCT modality and the fluorescence modality use the same fiber-based catheter 160.

The PIU 150 includes a non-illustrated beam combiner/splitter, a fiber optic rotary joint (FORJ) 152, and a pullback unit 151 (e.g., a precision linear stage). In one embodiment, the system too uses a swept-source laser (1310 nm+/−50 nm) as the OCT light source 110 for the OCT modality, and a Helium-Neon (He—Ne) laser with a center wavelength of about 633 nm as the excitation light source 180 for the fluorescence modality. The catheter 160 includes an imaging core comprised of a torque coil 163, a double clad fiber (DCF) 167 and a distal optics assembly 168. The imaging core is enclosed in a protective sheath 162 (shown in FIG. 2A). The distal optics assembly 168 may include a polished ball lens at the tip of the DCF 167 for side-view imaging. The distal optics assembly 168 may alternatively include a graded index (GRIN) lens and a beam directing component (e.g., a mirror, grating or prism) attached at the tip of the DCF 167. At the proximal end, the catheter 160 is removably connected to the PIU 150 via a catheter connector 161. In the fluorescence modality, the excitation light source 180 is connected to the PIU 150 via an optical fiber 181. The PIU 150 is controlled by the computer 200 to simultaneously deliver and collect radiation to/from a sample 170 via the catheter 160.

In operation, the imaging system 100 is configured to acquire co-registered OCT and fluorescence images from the sample 170 which may include a blood vessel, such as an artery or a vein. To that end, light or other electromagnetic radiation (radiation of first wavelength) from the OCT light source 110 is split in two parts, and one part guided through the sample arm 10 via the catheter 160 to the sample 170, and other part is guided through the reference arm 20 to a reflector 140. Thereafter, light reflected by the reflector 140 and light backscattered by the sample is collected to thereby generate an OCT interference signal. At the same time, light or other electromagnetic radiation (radiation of second wavelength) from the excitation light source 180 is guided through the fiber 181 to FORJ and to the sample 170, and a fluorescence signal (radiation of third wavelength) emitted from the sample 170 is collected via the catheter 160. The computer system 200 uses the OCT interference signal and the fluorescence signal to reconstruct an image of the sample 170.

Specifically, light from the light source 110 is split by a splitter 102 (e.g., a 50/50 fiber splitter or beam splitter) into a sample beam and a reference beam which are respectively conveyed to the sample arm 10 and the reference arm 20 via respective optical fibers. In the sample arm 10, the sample beam enters a circulator 105, passes to a single-mode (SM) fiber 106, and is delivered to the PIU 150. The catheter 160 is connected to the PIU 150, and the PIU 150 is in turn connected to computer 200 via non-illustrate connections such as a cable bundle. Under control of the computer 200, the PIU 150 controls rotation of the imaging core of catheter 160 to irradiate the sample 170 with the sample beam in a helical scanning manner. Light of the sample beam reflected and/or scattered by the sample 170 is collected by the distal optics 168 arranged at the distal end of the catheter 160, and the collected light is transmitted back through a double clad fiber 167 to the PIU 150. From the PIU 150 the collected light (sample beam) advances to the circulator 105 via the SM fiber 106. The circulator 105 guides the sample beam to the combiner 104.

In the reference arm 20, light of the reference beam enters a circulator 103 and is delivered to the reflector 140 via an optical fiber 141. In the case of Time Domain OCT (TD-OCT) imaging, the reflector 140 may be implemented as a scanning mirror. And, in the case of Frequency Domain OCT (FD-OCT) imaging, the reflector 140 may be implemented as a stationary mirror. Light of the reference beam reflected from the reflector 140 passes through the circulator 103, and is also guided to the combiner 104. In this manner, the sample and reference beams are combined at the beam combiner 104 where interference signals are generated according to known OCT principles. A detector 121 (a first detector) to detects the intensity of the interference signals.

The detector 121 can be a balanced detector implemented as an array of photodiodes, a photo multiplier tube (PMT), a multi-array of cameras or other similar interference pattern detecting device. The interference signals output from the first detector 121 are pre-processed by data acquisition electronics (DAQ1) 131, and transferred to the computer 200. The computer 200 performs signal processing to generate OCT images in a known manner. The interference patterns are generated only when the path length of the sample arm 10 matches the path length of the reference arm 20 within the coherence length of the OCT light source 110. In some embodiments, the sample arm 10 may include an optical delay line.

In the fluorescence modality, the excitation light source 180 emits excitation radiation (light) with a center wavelength of 633 nm (radiation of second wavelength) to irradiate the sample 170 through the PIU 150 and the distal optics of catheter 160. In response to being irradiated by the excitation light, the sample 170 emits near infrared auto-fluorescence (NIRAF signal) or near infrared fluorescence (NIRF signal) with broadband wavelengths of about 633 to 800 nm (radiation of third wavelength) based on known fluorescence emission principles. As used herein, fluorescence is an optical phenomenon in which the molecular absorption of energy in the form of photons triggers an immediate emission of fluorescent photons with a longer wavelength.

In one embodiment, the fluorescence signal generated by the sample 170 may include auto-fluorescence, which is the endogenous fluorescence light generated without application of a dye or an agent. In other embodiments, the fluorescence signal generated by the sample 170 may include fluorescence light generated by exogenous fluorescence of dye or contrast agents intravenously added to the lumen sample. The auto-fluorescence (or fluorescence) light is collected by the distal optics 168 of the catheter 160, and delivered back to the PIU 150, where the FORJ 152 and a non-illustrated beam combiner/splitter guides the fluorescence signal to a detector 122. The fluorescence signal (fluorescence intensity signal) output from detector 122 is digitized by data acquisition (DAQ) 132 and transmitted to the computer system 200 for image processing. Preferably, the OCT interference patterns of the OCT modality and the fluorescence signal from the fluorescence modality are delivered to the computer 100 simultaneously to be co-registered in terms of time and location.

As shown in FIG. 1, the computer 200 includes a central processing unit (CPU) 191, a storage memory (ROM/RAM) 192, a user input/output (I/O) interface 193, and a system interface 194. The various functional components of the computer 200 are operatively connected and communicate with each other via physical and logical data lines (e.g., a DATA BUS) 195. Storage memory 192 includes one or more computer-readable and/or writable media, and may include, for example, a magnetic disc (e.g., a hard disk drive HHD), an optical disc (e.g., a DVD®, a Blu-ray®, or the line), a magneto-optical disk, semiconductor memory (e.g., a non-volatile memory card, Flash® memory, a solid state drive, SRAM, DRAM), an EPROM, an EEPROM, etc. Storage memory 192 may store computer-readable data and/or computer-executable instructions including Operating System (OS) programs, and control and processing programs.

The user interface 193 provides a communication interface (electronic connections) to input/output (I/O) devices, which may include a keyboard, a display device (LCD or LED or OLED display) 300, a mouse, a printing device, a touch screen, a light pen, an external optical storage device, a scanner, a microphone, a camera, a drive, communication cable and a network (either wired or wireless). The system interface 194 also provides an electronic interface (electronic connection circuits) for one or more of the light source 110 of OCT modality, the excitation light source 180 of fluorescence modality, the detector unit 120, the DAQ unit 130, as well as the PIU 150. The system interface 194 may include programmable logic for use with a programmable logic device (PDL), such as a Field Programmable Gate Array (FPGA) or other PLD, discrete components, integrated circuitry (e.g., an Application Specific Integrated Circuit (ASIC)), or any other components including any combination thereof. The function of the user interface 193 and of the system interface 194 may be realized at least in part by computer executable instructions (e.g., one or more programs) recorded in storage memory 192 and executed by CPU 191, or programs executed in a remote location via a network (e.g. cloud computing). Moreover, the computer 200 may comprise one or more additional devices, for example, components such as a communications or network interface card for communicating with other medical devices, such as the PACS 350. The functional configuration of the imaging system 100 illustrated in FIG. 1 is implemented by the CPU 191 of computer 200 executing executable instructions or programs stored in the ROM/RAM of storage memory 192.

Referring again to FIG. 2A and FIG. 2B an exemplary pullback operation of the catheter 160 is briefly described as follows. The torque coil 163 delivers rotational torque from a non-illustrated rotational motor located in the PIU 150 to the distal optics assembly 168 arranged at distal end of the catheter, and the pullback unit 151 moves the catheter 160 linearly in the −z direction (pullback direction). Among the distal optics assembly 168, the beam directing component 165 (e.g., a mirror, a prism, or a grating) deflects irradiation light (illumination light beam 11) radially outward toward the sample 170 (wall of a lumen cavity) which is located at a lumen distance (LD). The illumination light beam 11 propagates from the distal end of the catheter 160 at an angle $\theta$ (theta) with respect to the catheter axis Ox, and is incident on the sample surface 171 at an incident angle $\beta$ (beta). The incident angle $\beta$ depends on the direction of the incident radiation (direction of beam 11) and the inclination of the sample surface 171. Therefore, since the sample surface 171 is not uniform, and the lumen distance (LD) from the catheter to the lumen wall is not constant, at each of a plurality of measurement points A1, A2, A3, A4, etc., along the lumen length, the incident angle $\beta$ can have different values $\beta_1$, $\beta_2$, $\beta_3$, $\beta_4$, etc. Here, since OCT data and fluorescence data are obtained simultaneously by the distal optics 168, illumination light beam 11 refers to light emitted by OCT light source 110 and/or light emitted from excitation light source 180 (i.e., light that irradiates the sample surface 171).

While the illumination beam ii (including OCT light and excitation light) illuminates the sample 170 (e.g., an artery), at least the imaging core of the catheter 160 rotates or oscillates (as indicated by arrow R) about the catheter axis Ox, while the imaging core is pulled back inside the sheath 162 (the sheath 162 remains substantially stationary). In this manner, the catheter 160 can continuously sweep the illumination beam ii in a helical rotary fashion through successive radial positions (as shown in FIG. 2B). The distal optics 168 collects a returning light 12 (sample beam) which includes OCT light backscattered from the sample and fluorescence light emitted by the sample 170. The returning light 12 carries information about the inner sample surface 171 (e.g., a vessel wall). An interference signal is detected by detector 121 when a reference light beam (not shown) is combined with the collected backscattered OCT light reflected from the sample. At the same time, the detector 122 detects the fluorescence signal, and transfers the detected value (intensity of the fluorescence signal) to the DAQ2 132 and computer 200. As explained above with reference to FIG. 1, the interference OCT signal and/or fluorescence signal are each independently converted into an electronic signal, which is then digitized, stored, and/or processed to analyze the status of the sample being examined.

The combination of backscattered light from the sample beam 12 and reference light from the reference beam (not shown) results in the interference signal, only if light from both the sample and reference beams have traveled substantially the same optical distance (where "substantially the same optical distance" indicates a difference of less than or equal to the coherence length of the light source). Regions of the sample 170 that reflect more light will create stronger interference signals than regions that reflect less light. Any light that is outside the coherence length will not contribute to the interference signal. The intensity profile of the reflected/backscattered light, which also referred to as an A-scan or an A-line scan, contains information about the spatial dimensions and location of characteristic features within the sample. An OCT image (generally referred to as a B-scan) may be formed by combining multiple adjacent A-line scans. The diagram of FIG. 2A depicts sequential measurements at positions A1, A2, A3, A4 along the length of the lumen sample during a pullback procedure of the catheter 160 at corresponding timings T1, T2, T3, T4, etc. Delta ($\delta$) represents a distance that the catheter travels during pullback in between successive one revolution measurements. Along the pullback path, the scanning of the sample 170 with the illumination light beam ii is considered to occur at a substantially fixed angle $\theta$, but it is to be understood that lumen distance (LD) and incident angle beta will not be constant because the surface 171 of the sample 170 is not uniform and the catheter does not remain concentric to the lumen.

FIG. 2B illustrates an axial view of the distal end of catheter 160 with exemplary illumination light beam 11 incident on the lumen sample 170 (e.g., blood vessel wall) at a plurality of locations R1, R2, R3, R4 along a helical path (this occurs while the catheter is rotated and pulled-back). Measurements at each rotational location are performed while scanning the sample 170 with a fixed (same) angle $\theta$. Each of locations R1, R2, R3, and R4 represents a different rotational location on the lumen inner surface at which a measurement is made while the catheter 160 rotates.

The pullback movement L combined with rotational movement R of the catheter 160 enables A-lines to be generated multiple times by helically scanning the inner surface 171 of the lumen sample 170. Combining the plurality of A-line scans allows the generating 2D images of the sample 170. Each 2D image of an artery cross section, for example, may be formed by approximately 500 or more A-line scans, corresponding to a full circumferential (360 degree) scan by the catheter 160. This full circumferential scan may be sometimes referred to as a "frame". Three-dimensional (3D) imaging of the inner surface 171 can be achieved by combining plural 2D image frames obtained during the longitudinal translational motion of the pullback operation while the catheter is rotating. The resulting catheter scan is a helical path of successive A-line scans to form 2D B-scans which can be combined into a full 3D dataset (or C-scan) of the sample 170. Each 360 degree rotation scan within the helical path may also be referred to as a frame, and multiple frames are generated along the longitudinal (z) axis in the minus z-direction. Data collected from successive A-line scans is processed (e.g., by fast Fourier transformation and other known algorithms) to generate OCT images of the sample 170 in a known manner. At the same time, the fluorescence signal (an intensity value) is also collected, processed (digitized and calibrated), displayed, and analyzed in correspondence with the OCT images.

<Display of Co-Registered Multi-Modality Lumen Images>

The results of pullback and image recording operations are typically displayed "as detected" for a user to evaluate the results. The display of fluorescence information (NIRAF or NIRF) and OCT data is automatically generated based on algorithmic processing techniques for overlaying the OCT and fluorescence data in predetermined formats. Catheter based multimodality imaging results can be shown as a ring of fluorescence data overlaid around the OCT tomographic view, and/or can be displayed to show the OCT and fluorescence data overlaid in longitudinal view (sometimes called carpet view).

More specifically, OCT and fluorescence data are automatically displayed on a two-dimensional map of the vessel revealing the structural characteristics of the vessel and the probability of presence of plaque and/or other chemical information within the vessel. In the longitudinal view, the two dimensional map may show the pullback position in millimeters on the x-axis and the circumferential position in degrees on the y-axis. For each pixel of a unit length and unit angle (e.g., 0.1 mm length and 1° angle), the amount of fluorescence is calculated from the spectral data collected and quantitatively coded on a color scale (or grayscale) in a range of values (e.g., 0 to 255) to represent shades of gray or percentages of the three primary colors (red, green, and blue). Whenever a pixel lacks sufficient data, for instance if there is a shadow or unexpected spike, the corresponding image pixel can be assigned a null value (e.g., black or white). The OCT and fluorescence data can also be displayed in a tomographic view to represent an axial view of the vessel at a selected location along the length of the vessel. In a tomographic view, the fluorescence data is mapped and paired with corresponding OCT data, and the fluorescence is displayed as a ring around the OCT image. Further details about various manners of displaying co-registered OCT and fluorescence image data are described in applicant's previous patent application publications including US 2019/0339850, US 2019/0029624, and US 2018/0271614 which are incorporated by reference herein for all purposes.

Advantageously, when catheter-based fluorescence is correlated with intraplaque characteristics or other feature characteristics determined from OCT data, it is possible to not only identify morphologically high-risk plaques, but also recognize pathobiologically regions of the vessel with enough accuracy to improve clinical results and provide better diagnostic outcomes for patient care. However, to ensure that data is correctly characterized, it is necessary to confirm appropriate detection and calibration of the catheter to lumen distance, and accurate detection of the fluorescence signal.

Within the multimodality OCT workflow, reliance on accurate spatial detection of vessel lumen—consisting of distance to the lumen from the optical probe and angle of the probe in relation to the lumen—is essential for use in accurate calibration, interrogation, and interpretation of the NIRAF signal.

NIRAF imaging relies on the excitation and emission of light by fluorophores—molecules in the imaging target (plaques and vessel wall) that auto-fluoresce when exposed to the excitation light emitted by the imaging core contained in the catheter arranged in the center of a vessel. The emitted fluorescence signal received at the catheter can be characterized by wavelength, amplitude, and lifetime of the signal to obtain information on the emitting fluorophore and generate a functional characteristic of the arterial wall and plaques. The excitation light and emission NIRAF signals are subject to absorption and scattering—caused by collision with non-fluorescent molecules along their path of travel—collectively referred to as attenuation. Attenuation obscures the relevant information carried by the NIRAF signal relating only to the auto-fluorescent response of a fluorophore to the excitation light. If factors such as the distance to the fluorophore, incident angle of the emission signal on the detector probe aperture, attenuation of the excitation signal, and attenuation of the emission signal are not controlled for via calibration, then characterization of the fluorescent tissue becomes inaccurate.

Co-localizing NIRAF and OCT signals significantly improves the diagnostic capabilities of both imaging techniques, by allowing the information typifying molecular and chemical composition of tissue provided by NIRAF to compliment the morphological information provided by OCT. Previous state of the art proposes using catheter to lumen distance and/or angle of incidence of the excitation light to the normal line to the sample surface to calibrate and synchronize the NIRAF signal with the morphological OCT signal. However, accurate location information of the sample surface is paramount to accurately calibrating the NIRAF signal by accounting for signal attenuation corresponding to NIRAF signal travel path length between the probe and fluorophore. Therefore, by eliminating the path length attenuation of the NIRAF signal as a factor in signal interpretation via calibration against this path length attenuation, the information carried by the emitted NIRAF signal can accurately characterize the fluorophore (meaning the amplitude, frequency, and lifetime of the fluorophore being characterized, rather than the fluorophore characteristic in addition to path length attenuation).

In this regard, it should be noted that fluorophores can be located at varying depths in the vessel wall and in plaques built-up at various locations of the vessel. However, in the method for calibration of NIRAF that uses lumen distance and/or incident angle, the current state-of-the art assumes that the fluorophore is located superficially on the lumen wall. Therefore, in order to accurately characterize the fluorophore, not only the distance to lumen wall alone and/or angle of incidence, but also the lumen morphology and fluorophore location must be known to accurate calibrate the NIRAF signal attenuation as a function of the signal path length to the fluorophore.

In the current state of the art, automatic lumen detection is chiefly relied upon to determine the signal path length to lumen from emission/detection probe and catheter, and if automatic detection of the lumen surface, depth, and angle is inaccurate, the resulting synchronization and calibration of the imaging signals will be inaccurate as well. Automatic lumen detection accuracy suffers in vessels that have irregular, non-uniform composition of lumen walls, where the lumen wall distance from the optical probe varies radially. In this environment, lumen depth is more appropriately expressed as a radial function (distance to lumen as a function of angle), and a manual override (among other partially automated methods) of the automated lumen detection would more accurately determine the distance to the lumen. Reliance solely on automatic lumen detection can potentially lead to lower fidelity NIRAF calibration, and the NIRAF reconstruction predicated on this calibration can still be inaccurate. A method for manual lumen wall identification, selection of a fluorescent region, or partially automated segmentation and manual selection of regions of interest in the vessel relevant to NIRAF calibration would increase the fidelity of calibration.

Therefore, according to one embodiment of the present disclosure, the MMOCT system is configured to correct inaccurate algorithmically-generated lumen detection by allowing the user to select portions of the lumen wall that do not match the lumen wall in the image generated from the OCT data, or by prompting the user to draw an enclosing hull or to drag an algorithmically-generated enclosing hull to match the lumen wall in the image generated from the OCT data. Given that the catheter and optics are localized to the center of the image, by manually generating an accurate lumen wall hull, the fluorescence signal can be calibrated against the distance and incident angle to the wall as a function of radial position (distance to the lumen wall varies with radial angle). Given that a user is generally experienced in lumen wall anatomy cases, the user's manual override of the algorithmically generated hull will provide better accuracy and improve both the calibration of the fluorescence signal and also the automated generation of information on the lumen, such as minimum and maximum diameter, lumen area, and mean diameter of the sample.

According to at least one embodiment, the MMOCT system also allows for manual selection of a region of interest (ROI) and identification of tissue types in the selected ROI corresponding with the user's knowledge of the appearance of specific tissue types in an OCT image. When an area of the OCT image is assigned a specific tissue type, the information of tissue type and its known optical attenuation can be factored into the calibration of the fluorescence signal that passes through this tissue, thereby improving the calibration of the fluorescence intensity.

FIGS. 3A through 3D illustrate an abbreviated version of the operating principle of the MMOCT catheter imaging a vessel of a patient. In an imaging operation of the MMOCT catheter, optical signals from both imaging modalities exit the catheter in a direction transversal (at an angle) to the catheter axis; at the same time, the catheter is rotated and pulled back through the lumen of the vessel. The optical signals travel through the fluid (blood and/or contrast agent) contained within the lumen, and these optical signals are incident on the vessel wall, on plaque built-up on the wall, and/or on lipid rich tissues within the vessel. At least part of the incident light travels (diffuses) through the various tissues that compose the vessel wall, all while being scattered, absorbed, reflected and/or re-emitted. The light collected by the catheter is detected by the detector unit 120, digitized by the DAQ unit 130, processed by the computer system 200, and stored in PACS 350 and/or displayed on display device 300.

Figure 3A:
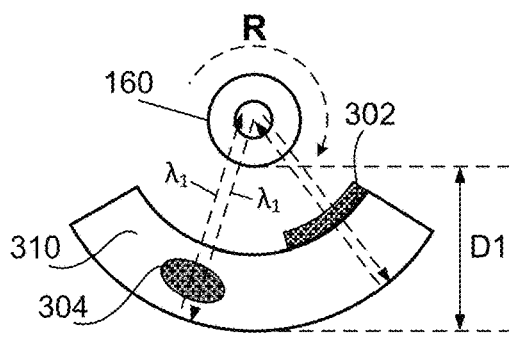
FIG. 3A and FIG. 3B respectively show OCT and NIRAF overlays of the same lumen cross-section with tissue artifacts suspended in the lumen of a vessel wall.
Figure 3B:
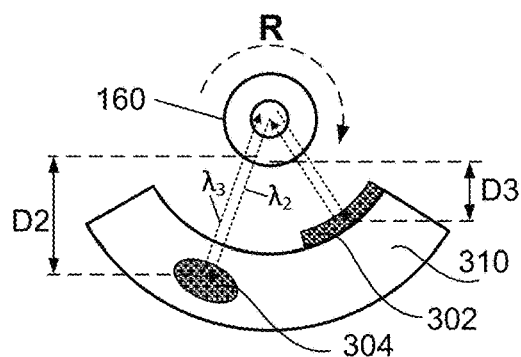

FIG. 3A and FIG. 3B show OCT and fluorescence overlays of the same lumen cross-section with tissue artifacts suspended in the lumen. The expression "tissue artifacts suspended in the lumen" is meant to indicate that when an artery is viewed in tomographic view, some damaged tissues (artifacts) that compose the artery cross section are seen by a cardiologist as suspended within plaque or possibly imbedded in the vessel wall. More specifically, the tissues that make-up a vessel wall are endothelial lining cells which form smooth muscle and connective tissues. These tissues are of interest to a cardiologist, and under a microscopic view the endothelial tissue would appear to the cardiologist as suspended in the lumen wall. Since medical understanding of the role of lipids and lipoproteins in the pathogenesis of atherosclerosis, as well as their critical roles in risk assessment can be improved by new imaging technologies, the MMOCT system according to the present disclosure provides morphological and pathological information about the normal tissue and suspended artifacts to more accurately calibrate the fluorescence signal.

FIG. 3A shows an example of intra-arterial microstructural and/or morphological catheter imaging using an OCT imaging modality. FIG. 3B shows an example of intra-arterial molecular and/or pathological imaging using a near infrared auto-fluorescence (NIRAF) imaging modality. These images are shown separately for the sake of convenience to better illustrate the imaging principles, but in reality the two images represent the same cross sectional view. In FIG. 3A, a radiation of first wavelength $\lambda 1$ is emitted radially from catheter 160, and travels through a vessel wall 310 to a depth of signal D1. The radiation of first wavelength $\mu 1$ may travel through a region of calcified plaque 302 and/or a lipid deposit 304 in the lining of the vessel all. In addition, the radiation of first wavelength may travel through contrast agent fluid (not shown) contained within the vessel wall 310 surrounding the catheter 160. The radiation of first wavelength will interact with (and will be scattered by) the contrast fluid, the calcified plaque 302, and/or the lipid deposit 304 and tissues of vessel wall 300 before being collected again by the catheter 160.

In FIG. 3B, a radiation of second wavelength $\lambda 2$ is emitted radially from catheter 160, travels through the contrast agent (not shown), is incident on the vessel wall 310 and travels to the lipid deposit 304. When the radiation of second wavelength $\lambda 2$ excites fluorophores contained in the lipid deposit 304, a radiation of third wavelength $\lambda 3$ (i.e., fluorescence light) is emitted from the lipid deposit 304. In this case, the radiation of second wavelength (excitation light) and the radiation of third wavelength (fluorescence light) have a signal path length D2. In FIG. 3B, the radiation of second wavelength $\lambda 2$ may also travel through the contrast agent (not shown), and be incident on the calcified plaque 302 built-up on the surface of vessel wall 310. When the radiation of second wavelength $\lambda 2$ excites the fluorophores contained in calcified plaque 302, a radiation of third wavelength $\lambda 3$ (i.e., fluorescence light) is emitted from the calcified plaque 302. In this case, the radiation of second wavelength (excitation light) and the radiation of third wavelength (fluorescence light) have a signal path length D3 which is smaller than the signal path length D2. In the sections of the vessel wall 310 where there are no sources of fluorescence (e.g., sections of the vessel without plaque or lipid deposits) the sample will not emit any radiation of third wavelength (fluorescence light) even if those sections are irradiated by the radiation of second wavelength (excitation light).

In other words, while the OCT light (radiation of first wavelength) will always interact with the vessel environment and provide a backscattered signal for every A-line scan, the excitation light (radiation of second wavelength) will only generate a fluorescence signal (radiation of third wavelength) when the excitation light interacts with a fluorescence source (e.g., fluorophores) present on the surface of the vessel wall or deep within the vessel tissue. Since the sources of fluorescence can be at different depths of the vessel wall, the radiation of third wavelength (fluorescent light) will have a signal intensity corresponding to the signal path length and/or the type of fluorescence source. Therefore, it is important to establish appropriate correlation of the location of a fluorescence source with the morphological features obtained from the OCT signal so that calibration of the fluorescence signal can be more accurately calculated.

Figure 3C:
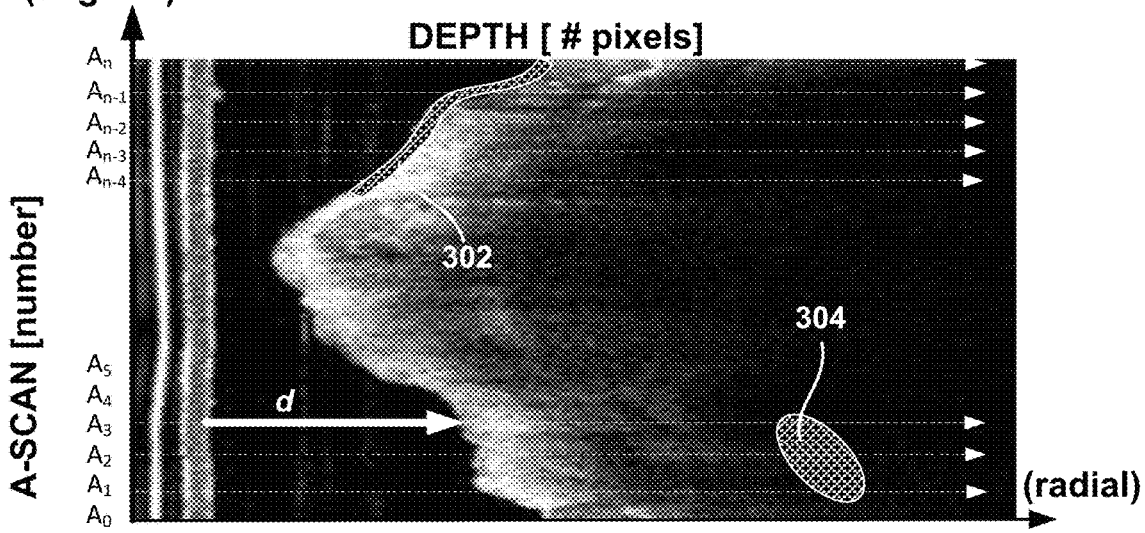
FIG. 3C illustrates an exemplary B-scan image reconstructed from a plurality of A-scans arranged in polar coordinates.

FIG. 3C illustrates an exemplary B-scan image reconstructed from a plurality of A-scans arranged in polar coordinates. As shown in FIG. 3C, the computer 200 of system 100 forms an image by arranging a plurality of A-line scans adjacent to each other, such that the number of A-scan on the vertical axis (y-axis) represent the angular scale from 0 to $2\pi$ and the signal path length (depth) is represented in the horizontal axis (x-axis). In FIG. 3C, the distance between the catheter and lumen edge of the vessel wall 310 is shown by the solid arrow d. The tissue region for calculation of optical attenuation property is calculated based on the detected intensity of the backscattering OCT signal received at the detector. Therefore, when considering the backscattered signal for A-line scans A1, A2, and A3, the intensity of the backscattered signals will be affected by optical attenuation of the tissue beyond the lumen edge and by the attenuation of the lipid deposit 304.

Figure 3D:
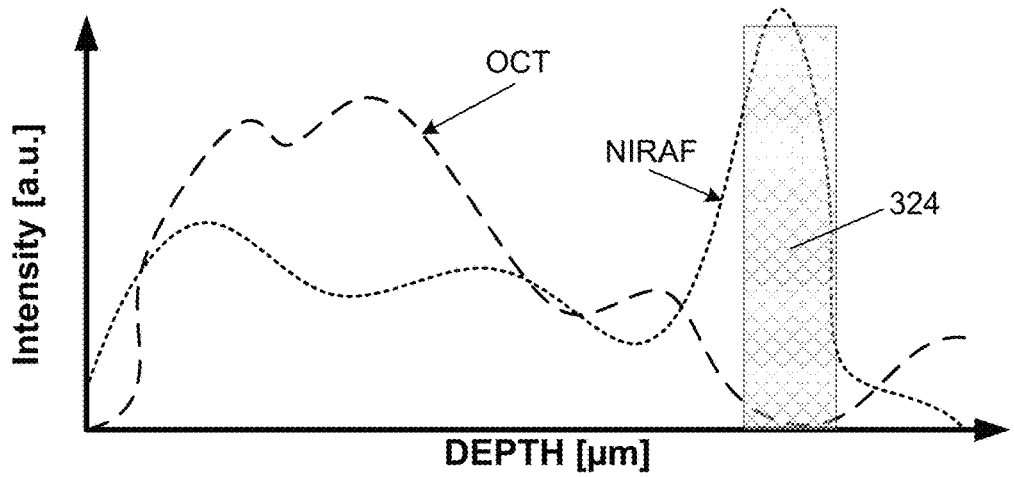
FIG. 3D shows a graph of tissue intensity profile at the cross-section of FIGS. 3A and 3B, according to an embodiment of the present disclosure.

FIG. 3D shows an example of the signal intensity profile in the depth direction of the OCT and NIRAF signals (not actual data). In FIG. 3D, it can be observed that in a region 324 corresponding to a depth where the lipid deposit 304 is located, the detected intensity of the OCT signal is low and the detected intensity of the NIRAF emission is high. Here, it should be noted that even if the lipid deposit 304 is at a location deep inside the vessel wall 310, the NIRAF signal is high because the strong emission of fluorescence from the lipid deposit. However, the OCT signal is low intensity because the OCT signal is attenuated by the lipid deposit. By using depth-resolved attenuation and backscatter coefficients from the OCT data to characterize tissue-type and correlating it with the fluorescence signal data from the same location, the fluorescence signal can be calibrated against attenuation from tissues in the NIRAF signal optical path that do not fluoresce.

Figure 4A:
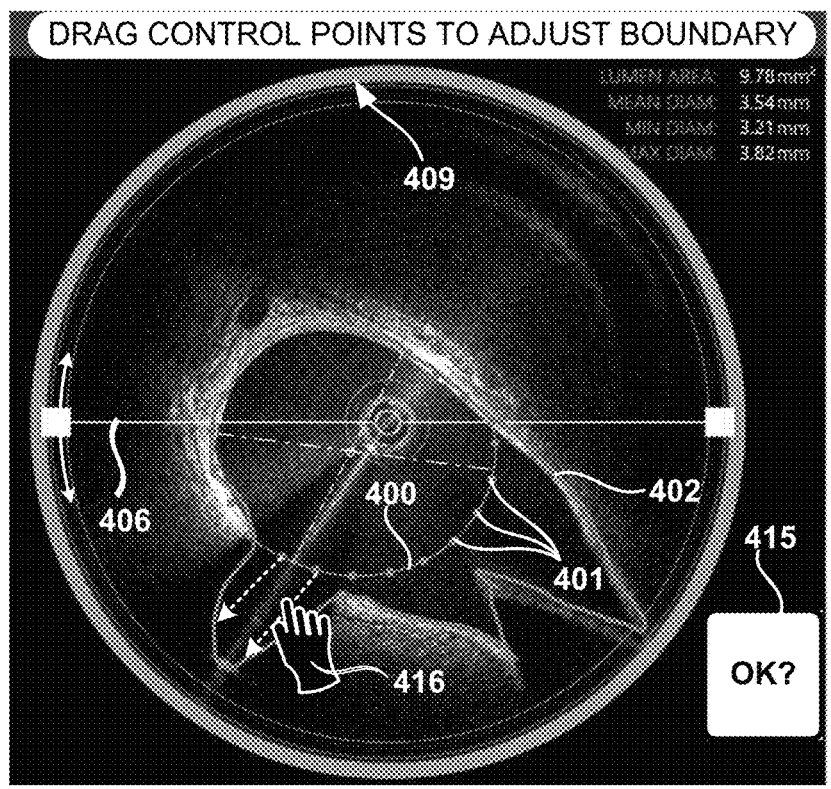
FIG. 4A and FIG. 4B show exemplary OCT and NIRAF co-registered images displaying both an algorithmically-generated lumen detection boundary line and a manual override line for cases where automated detection fails to produce an accurate lumen boundary, according to an embodiment of the present disclosure.
Figure 4B:
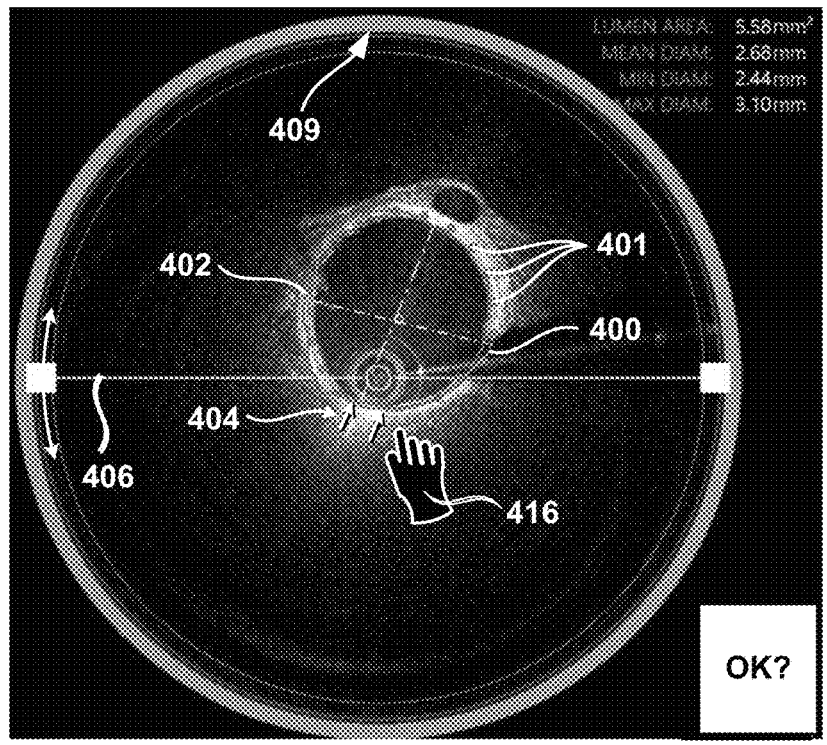

FIG. 4A and FIG. 4B show examples of how the manual override for lumen wall selection would manifest in a multimodality OCT/NIRAF imaging context. In FIG. 4A and FIG. 4B, the system automatically generates a tomographic OCT image 408 surrounded by a NIRAF signal 409, and also automatically generates a lumen boundary 400. This process is well known to persons having ordinary skill in the art. According to the present disclosure, the system is configured to generate the lumen boundary 400 in a manner that the user can manually edit and modify the lumen boundary. More specifically, FIG. 4A and FIG. 4B, show exemplary co-registered OCT and NIRAF images displaying both an algorithmically-generated lumen boundary 400 and a manually drawn lumen boundary line 402 for cases where the automated detection algorithm fails to produce an accurate lumen boundary.

This process allows a more accurate identification of structural composition (tissue, plaque, lipid deposit, etc.) for use in fluorescence signal calibration, based on OCT characteristics. The inventor's proposal is based on the understanding that, except for the NIRAF signal 409 around the edge of the tomographic view, the images shown in the center of FIG. 4A and FIG. 4B are generated from the OCT signal collected when the OCT light interacts with the vessel wall. In other words, OCT data is the source of the structural image in the MMOCT image. Therefore, in order to accurately identify the distinct layers of the vessel wall and structures contained in the vessel wall (e.g., plaque, blood/contrast agent, lipids, etc.), it is better (more advantageous) to rely on the OCT characteristics of the tissues or structural features that show-up in the structural image. However, an automated generated lumen sometimes fails to accurately define the lumen boundary.

FIG. 4A shows a scenario where the automated lumen detection may first define a lumen boundary 400. However, an experienced user might realize that the lumen boundary 400 does not match the actual structure of the vessels wall, and therefore can manually draw a new lumen boundary line 402 around the lumen wall structure in an artery with unusual geometry. To that end, the computer can be programmed to automatically draw a plurality control points 401 along the algorithm-generated lumen boundary. Then, the user can be prompted to confirm the accuracy of the algorithm-generated lumen boundary or can be prompted to edit the lumen boundary.

Similarly, FIG. 4B shows the same situation where the user may manually draw a new boundary line 402 around a lumen boundary 400 created by the automated lumen detection. The case of FIG. 4B shows a more usual artery geometry where the auto lumen algorithm failed appropriately recognize the lumen wall due to some circumstances. For example, the algorithm may have erroneously included a tissue region 404 as being part of the lumen. An error of this type may have been caused because the catheter is too close (touching) to the lumen edge, and the software cannot appropriately recognize the lumen edge. Therefore, an experienced user can manually draw a corrected lumen boundary line 402, so that the system can more accurately calibrate the NIRAF signal.

Figure 5:
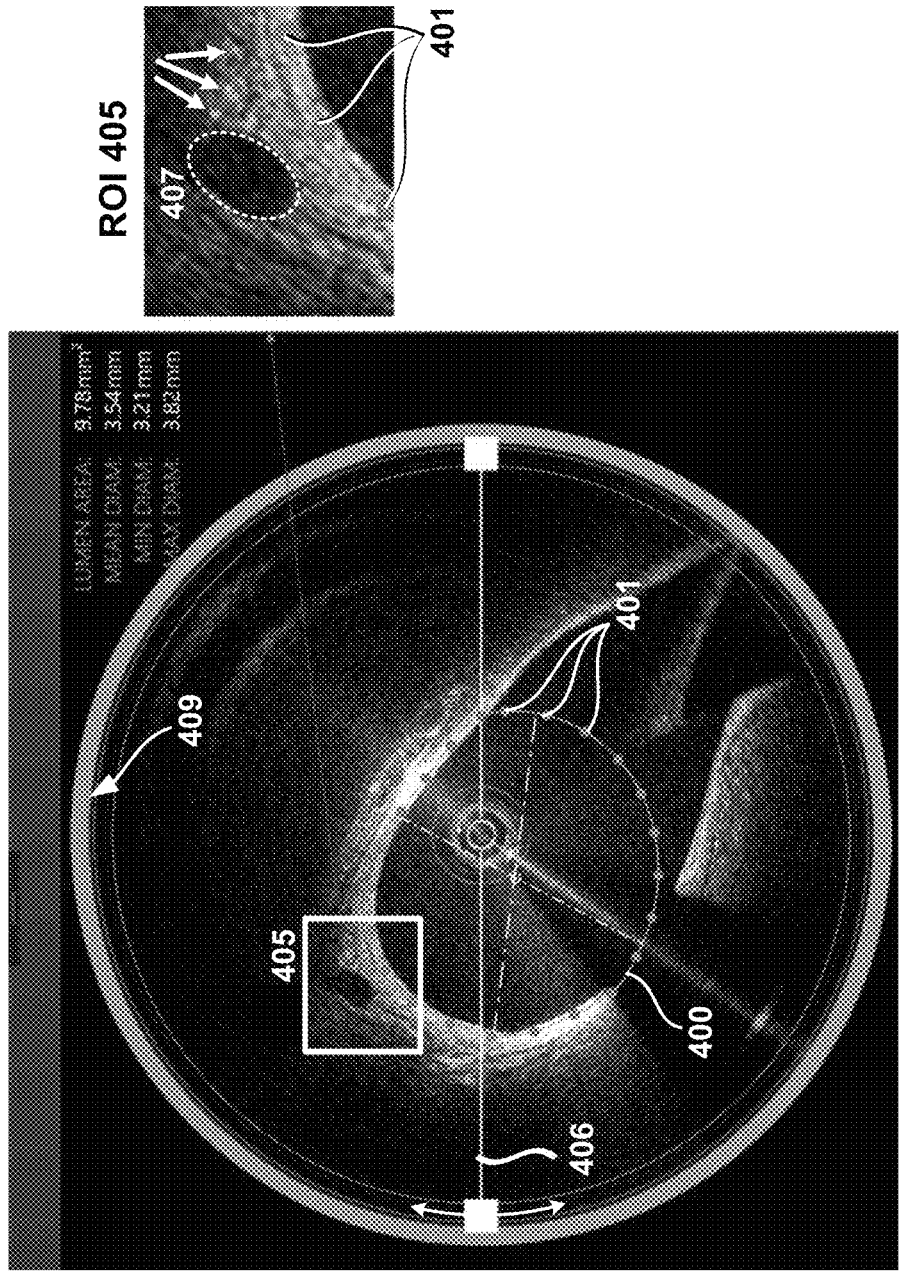
FIG. 5 shows an exemplary OCT and NIRAF co-registered image displaying an algorithmically-generated lumen boundary line 401 and a manually selected ROI 405, where the manual ROI selection allows the system to identify tissue composition for use in NIRAF calibration based on OCT characteristics, according to an embodiment of the present disclosure.

FIG. 5 illustrates exemplary co-registered OCT and NIRAF image displaying an algorithmically-generated lumen boundary 400 and a manually selected ROI 405. The manual selection of ROI 405 can be done by first moving a rotational control bar 406 to visually analyze sections of the MMOCT image with suspicious tissue features, and then using a pointer device (mouse) or touch screen tool 416 (as shown in FIG. 4A-4B). This allows the user to select specific features within the OCT image of the vessel wall for identification of tissue composition for use in NIRAF calibration based on OCT characteristics. The type of ROI can be defined by the user's input (e.g., a cardiologist's input) based on his/her experience about tissue types. For example, the selected ROI can be a distinct tissue type imbedded in the vessel wall that would likely have a different NIRAF characteristic than the surrounding endothelial/smooth muscles tissues, and thus would be important for NIRAF calibration. Manual selection/identification of the tissue ROI would improve the calibration of the NIRAF signal because the user is identifying exactly what is in the path of the NIRAF signal, and can apply the known effect of this tissue on NIRAF absorption/emission when accounting for the observed NIRAF signal at this radial position, thus improving NIRAF calibration.

<Manual Lumen Detection and ROI Selection>

When an automatically generated lumen boundary 400 is displayed on the screen of display 300, but the boundary is not matching with the actual edge of MMOCT image underneath, the present disclosure provides an interactive tool that allows the user to make corrections freely with few steps. More specifically, it is well known that in sterile environments of the medical field, it is impractical and difficult to use a pointer device such as a computer mouse to control imaging operations. Therefore, as shown in FIGS. 4A, 4B, and 5, the computer 200 is configured to generate the lumen boundary 400 with a plurality of dots or control points 401 represented in a distinct color or shape to be distinguishable over the colors of the MMOCT image (OCT and NIRAF). According to at least one embodiment of the present disclosure, it is advantageous to display the lumen edge boundary 400 in a manner that can facilitate editing operations by a user using a simple editing tool to reshape the contour of the lumen boundary 400. For example, after the user recognizes that the automatically generated lumen boundary 400 does not accurately match lumen edge of the vessel image, the GUI provides a fast and intuitive tool to help the user quickly reach the target in mind. To that end as shown in FIG. 4A and FIG. 4B, the user can use a touch-screen tool pointer 416 to individually select control points 401 which are not located at the true edge of the lumen. The user can interactively drag the control points 401 radially away from the center of lumen in a direction to increase the diameter of the lumen edge (as shown in FIG. 4A) or move the control points 401 radially towards the center of the lumen to reduce the diameter of the lumen edge (as shown in FIG. 4B). Notably, for severely irregular vessel walls as shown in FIG. 4A, the user can move the control points 401 in several directions to more accurately match the real edge of the lumen. Once the user is satisfied with the manual editing process a confirmation button 415 is used to accept the changes made.

In addition, the user may use touchscreen pointer tool 416 to draw geometric figures (e.g., squares, circles or triangles) or irregular shapes to manually select an ROI 405, as shown in FIG. 5. The computer 200 can be configured to maintain the MMOCT image unchanged while the user moves the control points 401 and/or selects the ROI 405. The confirmation button 415 can be provided by the GUI to allow the user to try different changes, and then only after the user is satisfied with the changes, the user can confirm that the changes are acceptable. And after confirmation, the computer 200 will accept the changes and apply the appropriate calibrations to the fluorescence signal according to the algorithm of FIG. 6. This interactive touchscreen tool 416 can provide simplified ways of a using a touch screen GUI by taking advantage of some gesture features and image annotation techniques which are well known in the art. See, for example, pre-grant patent application publication US 2020/0402646.

<Algorithm for Calibrating Fluorescence Based on Manual Lumen Detection>

Figure 6:
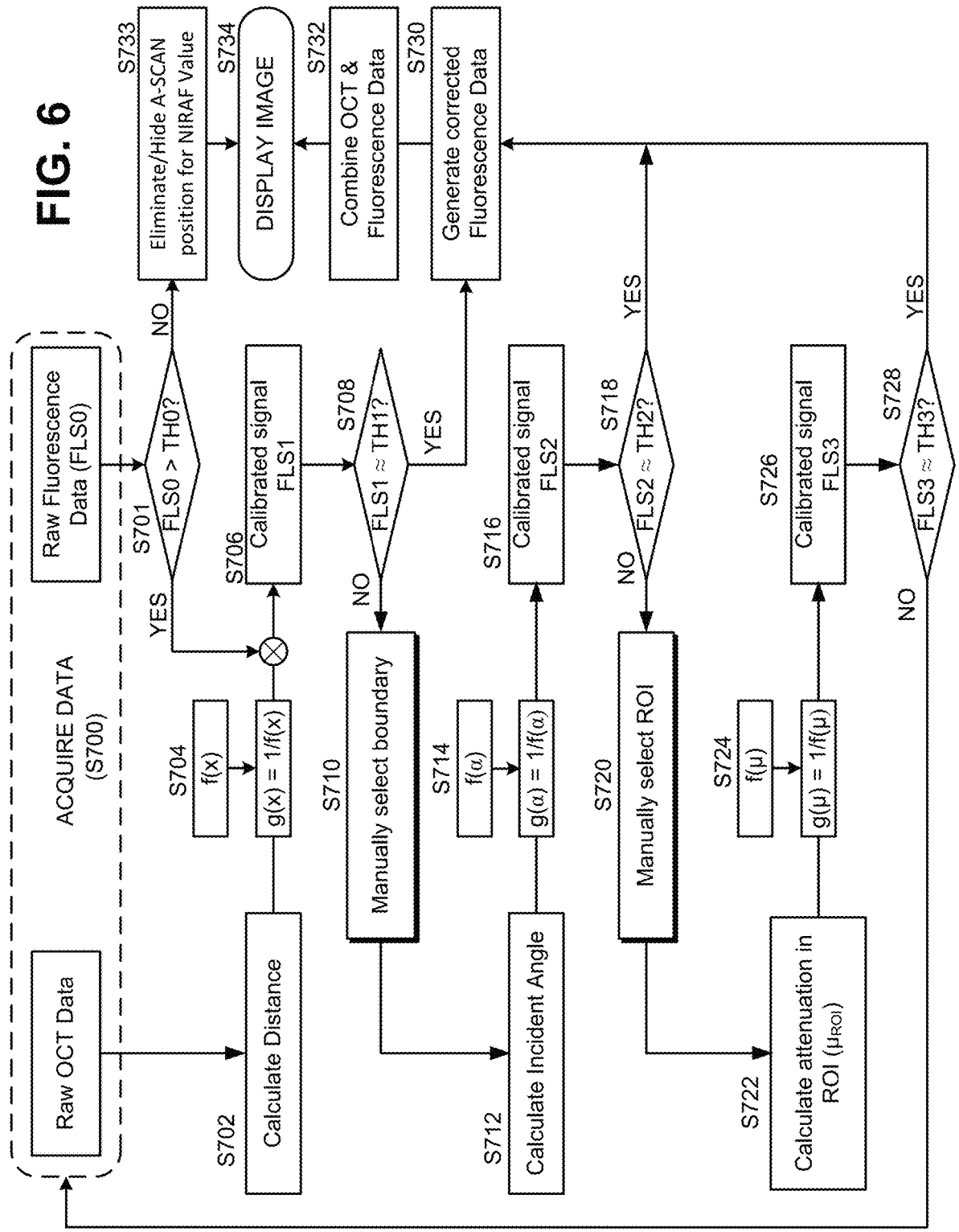
FIG. 6 shows an exemplary algorithm for fluorescence signal calibration that iteratively combines automatic and manual, or alternates automatic and manual, identification of the lumen wall in combination with manual ROI selection, according to an embodiment of the present disclosure.

FIG. 6 illustrates a functional block diagram of a signal processing algorithm for calibrating fluorescence data based on manual lumen detection and/or manual selection of regions of interest (ROI). The algorithm includes a "smart calibration" process based only on the raw NIRAF signal, and a "manual calibration" process based on OCT attenuation of manually detected lumen parameters and/or a manually selected ROI.

According to an embodiment, the multi-modality system too is configured to perform "Smart NIRAF calibration". Smart NIRAF calibration proposes to improve on the performance of computationally expensive process of NIRAF calibration, by executing calibration only at radial positions where detected NIRAF signal intensity stays above a determined threshold value and therefore NIRAF information will be displayed only at locations where calibration occurs. The disclosed workflow follows the idea that given a particular radial position has a NIRAF emission signal intensity above a specified calibration threshold, the calibration factor for this position based on any combination of the components of path travel as described above can be calculated and the NIRAF signal multiplied by this factor will be displayed radially. Here, it is important to note that "smart calibration" of the proposed workflow provides calibration only at radial positions where detected NIRAF signal intensity falls below a predetermined threshold value and therefore NIRAF information will be displayed only at locations where calibration occurs. This can reduce the amount of data that the user has to observer and analyze.

According to a further embodiment, fluorescence calibration is based on optical properties, such as attenuation of the OCT signal in a manually selected ROI and/or a manually redrawn lumen boundary. According to this embodiment, the multi-modality system is configured to determine/calculate calibration factor parameters (e.g., tissue composition and depth of signal) for a given radial position; this can be determined via radial OCT attenuation. Specific tissue types and molecular structures produce a characteristic OCT attenuation when normalized for signal travel distance (i.e., per a unit distance). Specifically, the amount of OCT signal not scattered or absorbed follows a specific characteristic for a specific tissue. Given a specific attenuation of a radial OCT signal, inferences based on known tissue optical coefficients can be made about the composition of the tissue that the OCT signal passes through.

The standard method for transformation of spectral-domain OCT data into the spatial domain to create an A-scan reveals the backscattering characteristics of the tissue in the optical path of the OCT signal. Research has been conducted into deriving depth-resolved backscatter and attenuation coefficients for human atrial tissues from the OCT image, with varying assumptions made about the relationship between backscattering and attenuation resulting in different methods for estimating the coefficients. See, for example, Shengnan Liu, et al., (Liu), "*Tissue characterization with depth-resolved attenuation coefficient and backscatter term in intravascular optical coherence tomography images*," J. Biomed. Opt. 22(9) 096004, 12 Sep. 2017. The method for estimation of coefficients discussed by Liu led to successful differentiation of 6 lumen vessel tissue types using OCT images. Here, the same techniques described by Liu for deriving depth-resolved backscatter and attenuation coefficients can be used to improve/enhance NIRAF calibration in the manual lumen detection and/or ROI selection. By determining the depth resolved coefficients for OCT, one can correlate an observed OCT signal with the type of tissues in that particular A-scan. Then, by knowing the tissues within a particular A-scan, this information can be used to calibrate the NIRAF signal at the same position. The benefit of using this information is the same for NIRAF calibration based on automatic and manual lumen selection. However, when the automated lumen detection does not consider the tissue a certain portion of the vessel wall or does not consider the tissue a certain ROI, it is advantageous to provide a tool to user, so that the user can manually select tissues that may not be included in the automatic calibration.

Referring back to FIG. 6, at step S700, the algorithm is applied to the raw data of each A-line scan or an average of A-line scans acquired during a pullback and image recoding operation. As noted above, the OCT-fluorescence imaging system performs OCT imaging and fluorescence imaging simultaneously to acquire co-registered OCT and NIRAF data. As an initial step, at step S701, the computer 200 of system 100 first analyzes the raw fluorescence data to determine if the initial fluorescence signal (FLS0) meets a minimum intensity threshold value (TH0). The minimum intensity threshold value can be based on the system limit of detection (LOD) value, or any system parameter related to the LOD. Here, during image processing, if the raw fluorescence signal intensity does not satisfy the LOD threshold (NO in S701), the process advances to step S733. At step S733, the system marks the area of the multimodality image corresponding to the A-line scan as an undefined area and eliminates (displays nothing for that A-scan position) in terms of NIRAF value. In other words, when the fluorescence signal intensity does not meet the system's LOD, the process advances to step S733 where the system outputs nothing (assigns a null value) for the NIRAF signal to be shown on the display 300 at step S734. On the other hand, when the raw fluorescence signal intensity is equal to or greater than the system's LOD (YES at S701), the process advances to the calibration procedure (step S706).

More specifically, at the same time as analyzing the raw fluorescence data, at step S702, the computer 200 also analyzes the OCT data to calculate or estimate a distance between the catheter and the edge of lumen (vessel wall). Here, one skilled in the art will recognize that the inner boundary of a vessel wall is also referred to as the lumen boundary of the vessel. As such, the term lumen boundary has been used interchangeably herein to refer to the inner surface or wall of the vessel. Calculating the catheter to lumen distance by analyzing an OCT image is well known, and it can be done in the same manner as disclosed in the applicant's previous patent application publications US 2019/0099079 and US 2019/0298174. In step S702, the computer 200 can be programmed to analyze intensities of the OCT signal backscattered from the vessel wall and detected by balanced photodetector 121 (see FIG. 1). In this process, one or more layers of the sample (a vessel wall) may be detected based on the intensities of the OCT signal (see FIG. 3A-FIG. 3D). The catheter to lumen distance (d) can be established as an average distance from the catheter to the one or more layers of the vessel, or it can be determined as the distance from the catheter to the first layer of the vessel in the radial direction (see FIG. 3C). The distance between the imaging catheter and the luminal surface can be measured using an automatic segmentation algorithm, for example, as described by Wang (referenced above). Then, at step S704, the computer 200 calculates a distance calibration factor $g(x)=1/f(x)$, where $f(x)$ is a distance calibration function. The distance calibration function $f(x)$ is an exponential fitting model where $f(x)=a*\exp(b*x)+c*\exp(d*x)$ which is applied for fitting the OCT signal corresponding to each A-line scan. The constants (a), (b), (c) and (d) are determined in the fitting process according to base reference values (ground truth values) or known attenuation properties for the type of tissue (e.g., calcified vs. non-calcified vessel tissue).

At step S706, the computer 200 applies (multiplies) the calibration factor g(x) to the raw fluorescence signal (FLS0). Therefore, the process of step S706 yields a first calibrated fluorescence signal (FLS1). The first calibrated fluorescence signal (FLS1) is a distance calibrated signal, which accounts for considering NIRAF calibration only at radial positions where the detected NIRAF signal intensity stays above a predetermined threshold value (e.g., the system limit of detection), and therefore NIRAF information will be displayed only at locations where calibration occurs.

At step S708, the computer 200 now determines if the first calibrated signal FLS1 satisfies a predetermined first threshold parameter TH1. The first threshold parameter TH1 can be a minimum or maximum radius expected for a given vessel sample; this minimum or maximum radius can be necessary to determine if the lumen distance is indeed at the first layer (or boundary) of the vessel sample. If the first calibrated signal FLS1 satisfies the predetermined first threshold parameter TH1 (YES at S708), the process advances to step S730. At step S730, the computer 200 outputs the corrected fluorescence data value. Then at step S732, the computer combines the OCT and the corrected fluorescence data. Thereafter, at step S734 the computer 200 displays the MMOCT image (OCT-NIRAF image) on display 300 showing NIRAF information only at locations where calibration occurs.

If the first calibrated signal FLS1 does not satisfy the predetermined first threshold parameter TH1 (NO at S708), the process advances to step S710. That is, if the first calibrated fluorescence signal does not satisfy a minimum or maximum radius expected for a given vessel sample, the process advances to step S710. At step S710, the system prompts the user to manually select a lumen boundary. As noted above, the first threshold parameter TH1 can be the minimum or maximum lumen radius or diameter of the vessel wall. However, this first threshold parameter TH1 is not limited to the radius or diameter of the vessel. Another parameter for the first threshold parameter TH1 can include the detection of vessel side branches, the detection of stent malapposition or underexpansion, and the like. Here, for example, the computer 200 can issue a prompt indicating to the user that an appropriate boundary for the sample has not been detected, or that the detected boundary is suspect, and that the user must manually select a lumen boundary (e.g., by clicking one or more control points 401 on the image). Therefore, at step S710, the computer generates a plurality of control points 401 along an approximate outline of the vessel diameter, and instructs the user to manually select (correct) at least part of the lumen boundary.

After the user has manually selected at least part of the lumen boundary, the process advances to step S712. At step S712, the computer 200 calculates an incident angle beta ($\beta$) at one or more points of the boundary newly selected (corrected) by the user. At step S714, the computer 200 calculates an angle calibration factor $g(\beta)$ based on an angle calibration function $f(\beta)$ The angle and its calibration factor $g(\beta)=1/f(\beta)$ can be calculated in the same manner as described in publication US 2019/0099079 previously disclosed by the assignee of the present application. At step S716, the computer 200 applies (multiplies) the angle calibration factor to the fluorescence signal FLS1. Therefore, the process of step S716 yields a second calibrated fluorescence signal (FLS2).

At step S718, the computer 200 now determines if the second calibrated signal FLS2 satisfies a predetermined second threshold (TH2). The second threshold TH2 can be determined as function of a minimum or maximum expected angle of incidence for irradiating a given sample. For example, for irradiating a biological lumen such as a vessel wall, the incident angle of radiation can be expected to be within a certain range of the normal to the sample surface. In this case, if the radiation is incident on the sample surface at the expected range of incident angles, the intensity of the calibrated signal FLS2 (second calibrated fluorescence signal) should satisfy the second threshold value TH2. Therefore, if the second calibrated signal FLS2 satisfies the predetermined second threshold value TH2 (YES at S718), the process advances to step S730.

Here too, at step S718, the second threshold TH2 is not limited to the incident angle. After the computer 200 applies (multiplies) the angle calibration factor to the fluorescence signal FLS1, the computer can compare the calibrated signal to other parameters (such as the amount of attenuation of the fluorescence signal) in addition to or instead of the predetermined second threshold value TH2.

If the second calibrated signal FLS2 does not satisfy the predetermined second threshold TH2 (NO at S718), the process advances to step S720. Examples of when the second calibrated signal FLS2 does not satisfy the predetermined second threshold TH2 (NO at S718) can include a situation where the signal corresponds to a vessel side branch or an irregular vessel shape (see FIG. 4) where the radiation is not incident on the sample surface at the expected range of incident angles.

At step S720, the computer 200 prompts the user to manually select a region of interest (ROI) within the image of the vessel sample. Here, the user may use its knowledge (familiarity) of tissue type, plaques, or other criteria to select a desired ROI. Alternatively, the computer 200 may provide a pointer or some kind of indication to inform the user of a recommended ROI (e.g., a region with unusually high signal attenuation) to be manually selected by the user.

Then, at step S722, the computer 200 calculates one or more optical properties of the tissue in the ROI selected by the user. The one or more optical properties are referred to herein as the "attenuation" of the region of interest ($\mu_{ROI}$) which degrades the optical signal traveling though the tissue in the ROI selected by the user. At step S724, the computer system calculates an attenuation calibration factor $g(\mu)$ based on an attenuation calibration function $f(\mu)$. The attenuation calibration function $f(\mu)$ is calculated using one or more attenuation factors such as signal absorption, signal diffusion, path length attenuation, etc. Herein, the attenuation calibration function $f(\mu)$ can be determined in the same manner as described in applicant's previous publication US 2019/0298174 which is incorporated by reference herein for all purposes.

At step S726, the computer system applies (multiplies) the attenuation calibration factor $g(\mu)$ to the already calibrated second fluorescence signal FLS2. Therefore, the step S726 yields a third fluorescence calibrated signal (FLS3). At step S728, the computer 200 again determines if the third calibrated signal FLS3 satisfies a predetermined third threshold (TH3). The third threshold TH3 can be determined as function of a maximum (or minimum) expected attenuation of the optical signal caused by the tissue in the selected ROI of a given sample. For example, in an ROI of a biological lumen such as a vessel wall, the attenuation of radiation can be determined based on whether the ROI includes one or more layers of tissue with plaque or not. In this case, if the ROI includes at least one layer of plaque, the intensity of the calibrated signal FLS3 (third calibrated fluorescence signal) should satisfy TH3 if sufficient fluorescence is emitted by such layer. Therefore, at S728, if the third calibrated signal FLS3 satisfies the predetermined third threshold TH3 (YES at S728), the process advances to step S730. At step S730, corrected fluorescence data is output or stored. Then, at step S732, the computer 200 combines the OCT data and the corrected (calibrated) fluorescence data in a known manner. Thereafter, the computer 200 displays the combined OCT-fluorescence image in an appropriate format.

If the third calibrated signal FLS3 does not satisfy the predetermined third threshold TH3 (NO at S728), the process returns to step S700, where the computer 200 analyzes the next A-scan or next frame of raw data. At step S702, the computer 200 repeats the process until the user can manually complete selecting the appropriate lumen boundary or can tryout all desired ROIs based on the user's experience and knowledge of the appearance of specific tissue types in the OCT image. Notably, as noted above, for the manually selected boundary and/or manually selected ROI, fluorescence data will be displayed only at locations where calibration occurs.

Given the ability to differentiate lumen vessel tissue types with an OCT image, the resulting tissue characterization estimations can be used to calibrate the fluorescence signal. By comparing the NIRAF calibration factor calculated using the aforementioned signal parameters of optical path length, incident angle with the depth of signal and tissue composition information obtained from the OCT characterization, the fluorescence signal can be fully calibrated iteratively to accurately reflect the auto fluorescence of fluorescent tissues while accounting for the attenuation of the excitation and emission signals by non-fluorescing tissues. Here, it is noted that this embodiment can be modified by using other morphological modality such as an IVUS modality, whereby tissue composition and depth of signal, can be determined from radial optoacoustic attenuation. In addition, other spectroscopy modality (e.g., diffuse optical spectroscopy or diffuse correlation spectroscopy) can be used, whereby tissue composition and depth of signal, can be determined from optical diffusion parameters.

General advantages provided by the above solutions manifest in the increase in fluorescence signal fidelity, meaning that the emission signal received from particular fluorescent molecules given a known excitation signal amplitude is highly characteristic of that molecule (meaning that the emission amplitude integrated over its life-time or the spectral shape of the signal received are known to be emitted from the molecule when absorbing the exact excitation signal input, with little deviation from this characteristic). Controlling for the attenuation of the fluorescence signals caused by scattering and path traveled through non-fluorescing tissue improves the fidelity of the fluorescence signal by conforming the signal more closely to what is emitted by the fluorescing molecule. Increasing NIRAF fidelity increases the diagnostic capability of the modality.

Beyond the increase in fidelity, by adhering to "smart" calibration methodology the calibration process is made less computationally complex. Selectively calibrating fluorescence intensity only in areas where the detected fluorescence signal meets a certain threshold requirement reduces the number of calibration computations performed because the system is configured to process only the manually selected boundary or ROI, but does not have to process the entire image. Some of the advantageous features disclosed herein include, but are not limited to, manual override selection of lumen wall, manual selection of calibration ROIs and identification of tissue composition, reducing NIRAF calibration computational complexity and processing time, NIRAF calibration based on OCT tissue characterization determined by signal attenuation parameters.

<Software Related Disclosure>

At least certain aspects of the exemplary embodiments described herein can be realized by a computer of a system or apparatus that reads out and executes computer executable instructions (e.g., one or more programs or executable code) recorded on a storage medium (which may also be referred to as a 'non-transitory computer-readable storage medium') to perform functions of one or more block diagrams or flowchart diagrams described above. The computer may include various components known to a person having ordinary skill in the art. For example, the computer may include signal processor implemented by one or more circuits (e.g., a field programmable gate array (FPGA) or an application specific integrated circuit (ASIC)) for performing the functions of one or more of the above-described embodiment(s), by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)), and may include a network of separate computers or separate processors to read out and execute the computer executable instructions. The computer executable instructions may be provided to the computer, for example, from a cloud-based network or from the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. The computer may include an input/output (I/O) interface to receive and/or send communication signals (data) to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

Other Embodiments and Modifications

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by persons of ordinary skill in the art to which this disclosure belongs. In that regard, breadth and scope of the present disclosure is not limited by the specification or drawings, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A catheter-based multi-modality imaging system, comprising:
a catheter configured to be inserted through a lumen of a vessel to guide radiation of two or more wavelengths to a vessel wall, and configured to simultaneously collect backscattered radiation in response to irradiating the vessel wall with a radiation of first wavelength and collect a fluorescence signal emitted by the vessel wall in response to irradiating the vessel wall with a radiation of second wavelength different from the first wavelength, wherein data of a first imaging modality and data of a second imaging modality are simultaneously acquired; and
a processor configured to:
compare the data of the first imaging modality to a first threshold;
in the event that the data of the first imaging modality is greater than the first threshold, combine the data of the second imaging modality with the data of the first imaging modality;
in the event that the data of the second imaging modality is less than or equal to the first threshold, eliminate the data of the second imaging modality for a scan position;
display an image of the vessel by overlaying first data corresponding to the collected backscattered radiation and second data corresponding to the collected fluorescence signal, wherein the first data shows a lumen boundary of the vessel wall and the second data shows the fluorescence signal in radial relation to the lumen boundary;
calculate, based on the first data, a lumen distance from the catheter to the vessel wall and/or an incident angle of the radiation incident on the vessel wall; and
generate a first calibrated fluorescence signal by applying a first calibration factor to the fluorescence signal based on the lumen distance and/or the incident angle;
wherein, if a parameter of the first calibrated fluorescence signal is different from an other threshold value, the processor is further configured to:
(i) receive a user selection of a portion of the lumen boundary and/or a region of interest (ROI) of the vessel wall,
(ii) calculate an optical attenuation property of the selected portion of lumen boundary and/or of the selected ROI based on the backscattered radiation collected from the vessel wall, and
(iii) generate a second calibrated fluorescence signal by applying a second calibration factor to the first calibrated fluorescence signal, the second calibration factor being based on the optical attenuation property of the selected portion of lumen boundary and/or of the selected ROI.

2. The catheter-based multi-modality imaging system according to claim 1,
wherein the processor is further configured to reconstruct an image of the vessel by combining data corresponding to the backscattered radiation and data corresponding to the first calibrated fluorescence signal and/or data corresponding to the second calibrated fluorescence signal, and
wherein the reconstructed image shows the data corresponding to the first calibrated fluorescence signal and/or the data corresponding to the second calibrated fluorescence signal in radial correspondence with the first image data only at radial locations where calibration of the fluorescence signal occurs.

3. The catheter-based multi-modality imaging system according to claim 1,
wherein the vessel wall includes vessel tissue comprising fluorophores located at varying depths, and
wherein the processor is configured to determine morphology parameters of the vessel wall and calibrate the first calibrated fluorescence signal based on an optical attenuation of the backscattered radiation as a function of a signal path length from the fluorophores to the lumen boundary.

4. The catheter-based multi-modality imaging system according to claim 1,
wherein the first imaging modality includes an optical coherence tomography (OCT) imaging modality or an intravascular ultrasound (IVUS) imaging modality, and the second imaging modality is fluorescence imaging modality, and
wherein the fluorescence imaging modality includes a near infrared auto fluorescence (NIRAF) imaging modality or a near infrared fluorescence (NIRF) imaging modality.

5. The catheter-based multi-modality imaging system according to claim 1,
wherein the processor is further configured to display a plurality of control points overlaid on the lumen boundary, and
wherein, in a case where one or more of the control points do not coincide with the lumen boundary, the processor is configured to prompt the user to move one or more of the control points to make all of the control points coincident with the lumen boundary of the vessel wall.

6. The catheter-based multi-modality imaging system according to claim 5,
wherein the processor calculates the optical attenuation property of the selected portion of lumen boundary, by calculating the optical attenuation of the backscattered radiation traveling from the vessel wall to the catheter through the one or more points moved to coincide with the lumen boundary.

7. The catheter-based multi-modality imaging system according to claim 6,
wherein the processor generates the second calibrated fluorescence signal by applying the second calibration factor to the first calibrated fluorescence signal, and
wherein the second calibration factor is based on the optical attenuation of the backscattered radiation traveling from the vessel wall to the lumen boundary and passing through the one or more points moved to coincide with the lumen boundary.

8. A catheter-based multi-modality imaging system, comprising:
a catheter configured to be inserted through a lumen of a vessel to guide radiation of two or more wavelengths to a vessel wall, and configured to simultaneously collect backscattered radiation in response to irradiating the vessel wall with a radiation of first wavelength and collect a fluorescence signal emitted by the vessel wall in response to irradiating the vessel wall with a radiation of second wavelength different from the first wavelength; and
a processor configured to:
display an image of the vessel by overlaying first data corresponding to the collected backscattered radiation and second data corresponding to the collected fluorescence signal, wherein the first data shows a lumen boundary of the vessel wall and the second data shows the fluorescence signal in radial relation to the lumen boundary;
calculate, based on the first data, a lumen distance from the catheter to the vessel wall and/or an incident angle of the radiation incident on the vessel wall; and
generate a first calibrated fluorescence signal by applying a first calibration factor to the fluorescence signal based on the lumen distance and/or the incident angle,
wherein the processor is further configured to display a plurality of control points overlaid on the lumen boundary, and
wherein, in a case where one or more of the control points does not coincide with the lumen boundary, the processor is configured to prompt the user to select a region of interest (ROI) near the one or more of the control points and calculate an optical attenuation of the backscattered radiation traveling from the vessel wall through the ROI to the one or more control points.

9. The catheter-based multi-modality imaging system according to claim 8, wherein the processor calculates the optical attenuation property of the selected portion of lumen boundary, by calculating the optical attenuation of the backscattered radiation traveling from the vessel wall to the catheter through the selected ROI to the lumen boundary.

10. A method of calibrating a fluorescence signal using images acquired by a catheter-based multi-modality imaging system, the method comprising:
inserting a catheter through a lumen of a vessel to guide radiation of two or more wavelengths to a vessel wall, and collecting backscattered radiation in response to irradiating the vessel wall with a radiation of first wavelength and collecting a fluorescence signal emitted by the vessel wall in response to irradiating the vessel wall with a radiation of second wavelength different from the first wavelength;
processing, by a processor, the backscattered radiation and the fluorescence signal collected from the vessel wall to form an image of the vessel;
displaying the image of the vessel by overlaying first data corresponding to the collected backscattered radiation and second data corresponding to the collected fluorescence signal, wherein the first data shows a lumen boundary of the vessel wall and the second data shows the fluorescence signal in radial relation to the lumen boundary;
calculating, based on the first data, a lumen distance from the catheter to the vessel wall and/or an incident angle of the radiation incident on the vessel wall;
generating a first calibrated fluorescence signal by applying a first calibration factor to the fluorescence signal based on the lumen distance and/or the incident angle; and
displaying a plurality of control points overlaid on the lumen boundary,
wherein, in a case where one or more of the control points do not coincide with the lumen boundary, prompting a user to move one or more of the control points to make all of the control points coincident with the lumen boundary of the vessel wall.

11. The method according to claim 10,
wherein the vessel wall includes vessel tissue comprising fluorophores located at varying depths, and
wherein the method further comprises determining morphology parameters of the vessel wall and calibrating the first calibrated fluorescence signal based on an optical attenuation of the backscattered radiation as a function of a signal path length from the fluorophores to the lumen boundary.

12. The method according to claim 10,
wherein the first imaging modality includes an optical coherence tomography (OCT) imaging modality or an intravascular ultrasound (IVUS) imaging modality, and the second imaging modality is fluorescence imaging modality, and
wherein the fluorescence imaging modality includes a near infrared auto fluorescence (NIRAF) imaging modality or a near infrared fluorescence (NIRF) imaging modality.

13. The method according to claim 10,
wherein, if a parameter of the first calibrated fluorescence signal is different from a threshold value,
(i) receiving from a selection of a portion of the lumen boundary and/or a region of interest (ROI) of the vessel wall,
(ii) calculating an optical attenuation property of the selected portion of lumen boundary and/or of the selected ROI based on the backscattered radiation collected from the vessel wall, and
(iii) generating a second calibrated fluorescence signal by applying a second calibration factor to the first calibrated fluorescence signal, the second calibration factor being based on the optical attenuation property of the selected portion of lumen boundary and/or of the selected ROI.

14. The method according to claim 13, further comprising:
reconstructing an image of the vessel by combining data corresponding to the backscattered radiation and data corresponding to the first calibrated fluorescence signal and/or data corresponding to the second calibrated fluorescence signal, and
displaying the reconstructed image to show the data corresponding to the first calibrated fluorescence signal and/or the data corresponding to the second calibrated fluorescence signal in radial correspondence with the first image data only at radial locations where calibration of the fluorescence signal occurs.

15. The method according to claim 13, further comprising:
calculating, by the processor, the optical attenuation property of the selected portion of lumen boundary, by calculating the optical attenuation of the backscattered radiation traveling from the vessel wall to the catheter through the one or more points moved to coincide with the lumen boundary.

16. The method according to claim 15, further comprising:
generating, by the processor, the second calibrated fluorescence signal by applying the second calibration factor to the first calibrated fluorescence signal,
wherein the second calibration factor is based on the optical attenuation of the backscattered radiation traveling from the vessel wall to the lumen boundary and passing through the one or more points moved to coincide with the lumen boundary.

17. The method according to claim 13, further comprising:
displaying a plurality of control points overlaid on the lumen boundary, and
wherein, in a case where one or more of the control points does not coincide with the lumen boundary, prompting the user to select an ROI near the one or more of the control points and calculating an optical attenuation of the backscattered radiation traveling from the vessel wall through the ROI to the one or more control points.

18. The method according to claim 17, further comprising:
calculating, by the processor, the optical attenuation property of the selected portion of lumen boundary, by calculating the optical attenuation of the backscattered radiation traveling from the vessel wall to the catheter through the selected ROI to the lumen boundary.

19. A non-transitory computer-readable medium configured to store instructions that when executed by one or more processors of a computing device, cause the computing device to perform the method according to claim 10.

* * * * *